(12) United States Patent
Härd et al.

(10) Patent No.: US 11,066,452 B2
(45) Date of Patent: Jul. 20, 2021

(54) ANTIBODY BINDING NANOFIBRILS

(71) Applicants: Torleif Härd, Uppsala (SE); Mats Sandgren, Uppsala (SE); Benjamin Schmuck, Uppsala (SE)

(72) Inventors: Torleif Härd, Uppsala (SE); Mats Sandgren, Uppsala (SE); Benjamin Schmuck, Uppsala (SE)

( * ) Notice: Subject to any disclaimer, the term of this patent is extended or adjusted under 35 U.S.C. 154(b) by 182 days.

(21) Appl. No.: 16/301,075

(22) PCT Filed: May 8, 2017

(86) PCT No.: PCT/SE2017/050461
§ 371 (c)(1),
(2) Date: Nov. 13, 2018

(87) PCT Pub. No.: WO2017/200461
PCT Pub. Date: Nov. 23, 2017

(65) Prior Publication Data
US 2019/0161521 A1    May 30, 2019

(30) Foreign Application Priority Data
May 17, 2016 (SE) .................................. 1650661-0

(51) Int. Cl.
| G01N 33/531 | (2006.01) |
| C07K 14/395 | (2006.01) |
| C07K 14/31 | (2006.01) |
| C07K 16/00 | (2006.01) |
| C07K 1/22 | (2006.01) |
| C07K 16/06 | (2006.01) |

(52) U.S. Cl.
CPC .............. *C07K 14/395* (2013.01); *C07K 1/22* (2013.01); *C07K 14/31* (2013.01); *C07K 16/00* (2013.01); *C07K 16/065* (2013.01); *G01N 33/531* (2013.01); *C07K 2319/00* (2013.01); *C07K 2319/30* (2013.01)

(58) Field of Classification Search
CPC .... C07K 14/395; C07K 16/00; C07K 16/065; C07K 2319/30; C07K 2319/00; G01N 33/531; G01N 33/54346
See application file for complete search history.

(56) References Cited

FOREIGN PATENT DOCUMENTS

| CN | 101624568 A | 1/2010 |
| WO | 00/75324 A2 | 12/2000 |
| WO | 2005/118633 A2 | 12/2005 |
| WO | 2008/033451 A2 | 3/2008 |
| WO | 2016/034728 A1 | 3/2016 |

OTHER PUBLICATIONS

Janeway et al. The Immune System in Health and Disease. 5th edition. New York: Garland Science; 2001. The distribution and functions of immunoglobulin isotypes. (Year: 2001).*
Choe et al. (Materials 2016 9:994 Total 17 pages) (Year: 2016).*
Anderson et al. Journal of Histochemistry & Cytochemistry 2013 vol. 61: 773-784 (Year: 2013).*
Lee, Dae-Sung et. al., A protein nanofiber hydrogel for sensitive immunoassays, Analyst, vol. 138, pp. 4786-4794 (2013).
Men, Dong et al., Seeding-Induced Self-assembling Protein Nanowires Dramatically Increase the Sensitivity of Immunoassays, Nano Letters, vol. 9, No. 6, pp. 2246-2250 (2009).
Men, Dong et al., An auto-biotinylated bifunctional protein nanowire for ultra-sensitive molecular biosensing, Biosensors and Bioelectronics, vol. 26, pp. 1137-1141 (2010).
Leng, Yan et al., Integration of a Fluorescent Molecular Biosensor into Self-Assembled Protein Nanowires: A Large Sensitivity Enhancement, Angew. Chem. Ed., vol. 49, pp. 7243-7246 (2010).
Ghose, Sanchayita et al., Binding Capacity Differences for Antibodies and Fc-Fusion Proteins on Protein A Chromatographic Materials, Biotechnology and Bioengineering, vol. 96, No. 4, pp. 768-779 (Mar. 1, 2007).
Ghisaidoobe, Amar BT et al., Functionalized protein nanocages as a platform of targeted therapy and immunodetection, Nanomedicine (Lond.), vol. 10, No. 24, pp. 3579-3595 (2015).
Hauser, Charlotte A. E., Amyloid-based nanosensors and nanodevices, Chem. Soc. Rev., vol. 43, pp. 5326-5345 (2014).
Nelson, Justin T. et al., Mechanism of Immobilized Protein A Binding to Immunoglobulin G on Nanosensor Array Surfaces, Anal. Chem., vol. 87, pp. 8186-8193 (2015).
Schmuck, Benjamin, A fine-tuned composition of protein nanofibrils yields an upgraded functionality of displayed antibody binding domains, Biotechnol. J., vol. 12, 1600672, pp. 1-14 (Apr. 3, 2017).
Hudalla, Gregory A. et al., Gradated assembly of multiple proteins into supramolecular nanomaterials, Nature Materials, vol. 13, No. 8, pp. 829-836 (Aug. 1, 2014).
Scheibel, Thomas, Protein fibers as performance proteins: new technologies and applications, Current Opinion in Biotechnology, vol. 16, No. 4, pp. 427-433 (2005).
Supplementary European Search Report dated Jan. 14, 2020 from corresponding European Application No. 17799765.7.

\* cited by examiner

*Primary Examiner* — Changhwa J Cheu
(74) *Attorney, Agent, or Firm* — Proter Wright Morris & Arthur LLP

(57) ABSTRACT

The present embodiments relate to antibody binding nanofibrils obtainable by co-fibrillation of carrier proteins and carrier-Z fusion proteins at a molar ratio selected within an interval of from 1:0.20 to 1:0.90. The antibody binding nanofibrils have extremely high antibody binding capacity and can thereby be used in various applications, such as antibody purification, and detection of biomarkers in point of care or laboratory diagnosis applications.
(FIG. 6).

Figure 1:
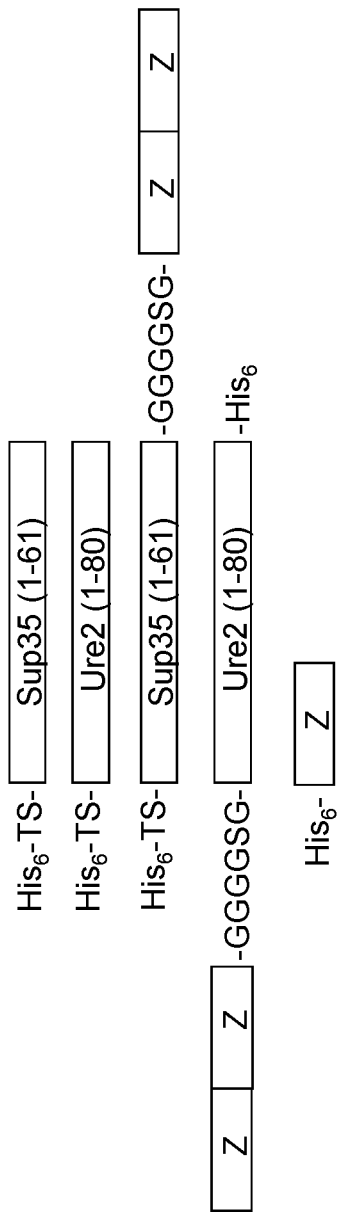

30 Claims, 10 Drawing Sheets
Specification includes a Sequence Listing.

SEQUENCE LISTING

```
<160> NUMBER OF SEQ ID NOS: 12

<210> SEQ ID NO 1
<211> LENGTH: 7
<212> TYPE: PRT
<213> ORGANISM: Artificial Sequence
<220> FEATURE:
<223> OTHER INFORMATION: Alpha helix motif
<220> FEATURE:
<221> NAME/KEY: HELIX
<222> LOCATION: (2)..(6)
<223> OTHER INFORMATION: Repeated 2 to 5 times

<400> SEQUENCE: 1

Ala Glu Ala Ala Ala Lys Ala
1               5

<210> SEQ ID NO 2
<211> LENGTH: 5
<212> TYPE: PRT
<213> ORGANISM: Artificial Sequence
<220> FEATURE:
<223> OTHER INFORMATION: Flexible linker
<220> FEATURE:
<221> NAME/KEY: REPEAT
<222> LOCATION: (1)..(5)
<223> OTHER INFORMATION: Repeates 5 to 7 times

<400> SEQUENCE: 2

Gly Gly Gly Gly Ser
1               5

<210> SEQ ID NO 3
<211> LENGTH: 5
<212> TYPE: PRT
<213> ORGANISM: Artificial Sequence
<220> FEATURE:
<223> OTHER INFORMATION: Flexible linker
<220> FEATURE:
<221> NAME/KEY: REPEAT
<222> LOCATION: (1)..(5)
<223> OTHER INFORMATION: Repeated 5 to 7 times
```

```
<400> SEQUENCE: 3

Gly Gly Gly Gly Thr
1               5

<210> SEQ ID NO 4
<211> LENGTH: 29
<212> TYPE: PRT
<213> ORGANISM: Artificial Sequence
<220> FEATURE:
<223> OTHER INFORMATION: Flexible linker

<400> SEQUENCE: 4

Gly Ser Ala Gly Ser Ala Ala Gly Ser Gly Glu Phe Gly Gly Gly Gly
1               5                   10                  15

Ser Gly Ser Ala Gly Ser Ala Ala Gly Ser Gly Glu Phe
            20                  25

<210> SEQ ID NO 5
<211> LENGTH: 29
<212> TYPE: PRT
<213> ORGANISM: Artificial Sequence
<220> FEATURE:
<223> OTHER INFORMATION: Flexible linker

<400> SEQUENCE: 5

Gly Ser Ala Gly Ser Ala Ala Gly Ser Gly Glu Phe Gly Gly Gly Gly
1               5                   10                  15

Thr Gly Ser Ala Gly Ser Ala Ala Gly Ser Gly Glu Phe
            20                  25

<210> SEQ ID NO 6
<211> LENGTH: 27
<212> TYPE: PRT
<213> ORGANISM: Artificial Sequence
<220> FEATURE:
<223> OTHER INFORMATION: Flexible linker with helix motif
<220> FEATURE:
<221> NAME/KEY: HELIX
<222> LOCATION: (12)..(16)
<223> OTHER INFORMATION: Repeated 2 to 3 times

<400> SEQUENCE: 6

Gly Gly Gly Gly Ser Gly Gly Gly Gly Ser Ala Glu Ala Ala Ala Lys
1               5                   10                  15

Ala Gly Gly Gly Gly Ser Gly Gly Gly Gly Ser
            20                  25

<210> SEQ ID NO 7
<211> LENGTH: 27
<212> TYPE: PRT
<213> ORGANISM: Artificial Sequence
<220> FEATURE:
<223> OTHER INFORMATION: Flexible linker with helix motif
<220> FEATURE:
<221> NAME/KEY: HELIX
<222> LOCATION: (12)..(16)
<223> OTHER INFORMATION: Repeated 2 to 3 times

<400> SEQUENCE: 7

Gly Gly Gly Gly Thr Gly Gly Gly Gly Thr Ala Glu Ala Ala Ala Lys
1               5                   10                  15

Ala Gly Gly Gly Gly Thr Gly Gly Gly Gly Thr
            20                  25
```

```
<210> SEQ ID NO 8
<211> LENGTH: 31
<212> TYPE: PRT
<213> ORGANISM: Artificial Sequence
<220> FEATURE:
<223> OTHER INFORMATION: Flexible linker with helix motif
<220> FEATURE:
<221> NAME/KEY: HELIX
<222> LOCATION: (14)..(18)
<223> OTHER INFORMATION: Repeated 2 to 3 times

<400> SEQUENCE: 8

Gly Ser Ala Gly Ser Ala Ala Gly Ser Gly Glu Phe Ala Glu Ala Ala
1               5                   10                  15

Ala Lys Ala Gly Ser Ala Gly Ser Ala Ala Gly Ser Gly Glu Phe
            20                  25                  30

<210> SEQ ID NO 9
<211> LENGTH: 327
<212> TYPE: PRT
<213> ORGANISM: Artificial Sequence
<220> FEATURE:
<223> OTHER INFORMATION: His6-Trombin site-Sup35(1-61)
<220> FEATURE:
<221> NAME/KEY: METAL
<222> LOCATION: (5)..(10)
<223> OTHER INFORMATION: His6-tag
<220> FEATURE:
<221> NAME/KEY: DOMAIN
<222> LOCATION: (14)..(19)
<223> OTHER INFORMATION: Thrombin cleavage site

<400> SEQUENCE: 9

Met Gly Ser Ser His His His His His His Ser Ser Gly Leu Val Pro
1               5                   10                  15

Arg Gly Ser His Met Ser Asp Ser Asn Gln Gly Asn Asn Gln Gln Asn
            20                  25                  30

Tyr Gln Gln Tyr Ser Gln Asn Gly Asn Gln Gln Gln Gly Asn Asn Arg
        35                  40                  45

Tyr Gln Gly Tyr Gln Ala Tyr Asn Ala Gln Ala Gln Pro Ala Gly Gly
50                  55                  60

Tyr Tyr Gln Asn Tyr Gln Gly Tyr Ser Gly Tyr Gln Gln Gly Gly Tyr
65                  70                  75                  80

Gln Ala Thr Gly Gly Cys Ala Gly Cys Ala Gly Cys Cys Ala Thr
                85                  90                  95

Cys Ala Thr Cys Ala Thr Cys Ala Thr Cys Ala Thr Cys Ala Cys Ala
            100                 105                 110

Gly Cys Ala Gly Cys Gly Gly Cys Cys Thr Gly Gly Thr Gly Cys Cys
        115                 120                 125

Gly Cys Gly Cys Gly Gly Cys Ala Gly Cys Cys Ala Thr Ala Thr Gly
    130                 135                 140

Thr Cys Ala Gly Ala Cys Thr Cys Ala Ala Cys Cys Ala Ala Gly Gly
145                 150                 155                 160

Gly Cys Ala Ala Cys Ala Ala Cys Cys Ala Gly Cys Ala Ala Ala Ala
            165                 170                 175

Cys Thr Ala Thr Cys Ala Ala Cys Ala Ala Thr Ala Cys Ala Gly Cys
        180                 185                 190

Cys Ala Ala Ala Ala Cys Gly Gly Cys Ala Ala Cys Cys Ala Gly Cys
    195                 200                 205

Ala Gly Cys Ala Gly Gly Gly Cys Ala Ala Cys Ala Ala Cys Cys Gly
    210                 215                 220
```

-continued

```
Cys Thr Ala Cys Cys Ala Gly Gly Cys Thr Ala Thr Cys Ala Ala
225                 230                 235                 240

Gly Cys Thr Thr Ala Cys Ala Ala Cys Gly Cys Cys Ala Ala Gly
            245                 250                 255

Cys Gly Cys Ala Gly Cys Cys Ala Gly Cys Ala Gly Gly Thr Gly
            260                 265                 270

Cys Thr Ala Thr Thr Ala Cys Cys Ala Gly Ala Ala Thr Ala Thr
            275                 280                 285

Cys Ala Ala Gly Gly Thr Thr Ala Cys Thr Cys Ala Gly Gly Cys Thr
            290                 295                 300

Ala Thr Cys Ala Ala Cys Ala Gly Gly Thr Gly Gly Cys Thr Ala
305                 310                 315                 320

Cys Cys Ala Ala Thr Ala Ala
            325
```

<210> SEQ ID NO 10
<211> LENGTH: 403
<212> TYPE: PRT
<213> ORGANISM: Artificial Sequence
<220> FEATURE:
<223> OTHER INFORMATION: His6-Trombin site-Ure2(1-80)
<220> FEATURE:
<221> NAME/KEY: METAL
<222> LOCATION: (5)..(10)
<223> OTHER INFORMATION: His6-tag
<220> FEATURE:
<221> NAME/KEY: DOMAIN
<222> LOCATION: (14)..(19)
<223> OTHER INFORMATION: Thrombin cleavage site

<400> SEQUENCE: 10

```
Met Gly Ser Ser His His His His His His Ser Ser Gly Leu Val Pro
1               5                   10                  15

Arg Gly Ser His Met Met Asn Asn Asn Gly Asn Gln Val Ser Asn Leu
                20                  25                  30

Ser Asn Ala Leu Arg Gln Val Asn Ile Gly Asn Arg Asn Ser Asn Thr
            35                  40                  45

Thr Thr Asp Gln Ser Asn Ile Asn Phe Glu Phe Ser Thr Gly Val Asn
        50                  55                  60

Asn Asn Asn Asn Asn Asn Ser Ser Ser Asn Asn Asn Val Gln Asn
65                  70                  75                  80

Asn Asn Ser Gly Arg Asn Gly Ser Gln Asn Asn Asp Asn Glu Asn Asn
                85                  90                  95

Ile Lys Asn Thr Ala Thr Gly Gly Gly Cys Ala Gly Cys Ala Gly Cys
            100                 105                 110

Cys Ala Thr Cys Ala Thr Cys Ala Thr Cys Ala Thr Cys Ala Thr Cys
            115                 120                 125

Ala Cys Ala Gly Cys Ala Gly Cys Gly Gly Cys Cys Thr Gly Gly Thr
            130                 135                 140

Gly Cys Cys Gly Cys Gly Cys Gly Gly Cys Ala Gly Cys Cys Ala Thr
145                 150                 155                 160

Ala Thr Gly Ala Thr Gly Ala Ala Thr Ala Ala Thr Ala Ala Cys Gly
            165                 170                 175

Gly Cys Ala Ala Cys Cys Ala Gly Gly Thr Gly Thr Cys Ala Ala
            180                 185                 190

Cys Thr Thr Gly Thr Cys Ala Ala Ala Thr Gly Cys Thr Thr Ala
            195                 200                 205

Cys Gly Cys Cys Ala Gly Gly Thr Cys Ala Ala Thr Ala Thr Cys Gly
```

```
            210                 215                 220
Gly Cys Ala Ala Thr Ala Gly Ala Ala Cys Thr Cys Cys Ala Ala
225                 230                 235                 240

Thr Ala Cys Thr Ala Cys Cys Ala Cys Ala Gly Ala Thr Cys Ala Gly
                245                 250                 255

Ala Gly Thr Ala Ala Cys Ala Thr Cys Ala Ala Cys Thr Thr Cys Gly
                260                 265                 270

Ala Ala Thr Thr Cys Thr Cys Cys Ala Cys Gly Gly Thr Gly Thr
                275                 280                 285

Thr Ala Ala Thr Ala Ala Thr Ala Ala Thr Ala Cys Ala Ala Cys
                290                 295                 300

Ala Ala Cys Ala Ala Thr Thr Cys Thr Thr Cys Ala Ala Gly Cys Ala
305                 310                 315                 320

Ala Cys Ala Ala Cys Ala Ala Cys Ala Ala Cys Gly Thr Gly Cys Ala
                325                 330                 335

Ala Ala Ala Cys Ala Ala Cys Ala Ala Cys Thr Cys Gly Gly Gly Thr
                340                 345                 350

Cys Gly Thr Ala Ala Thr Gly Gly Cys Thr Cys Thr Cys Ala Gly Ala
                355                 360                 365

Ala Cys Ala Ala Cys Gly Ala Thr Ala Ala Cys Gly Ala Ala Ala Ala
                370                 375                 380

Cys Ala Ala Cys Ala Thr Cys Ala Ala Gly Ala Ala Cys Ala Cys Ala
385                 390                 395                 400

Thr Ala Ala
```

<210> SEQ ID NO 11
<211> LENGTH: 815
<212> TYPE: PRT
<213> ORGANISM: Artificial Sequence
<220> FEATURE:
<223> OTHER INFORMATION: His6-Trombin site-Sup35(1-61)-GGGSG linker-Z
      Homodimer
<220> FEATURE:
<221> NAME/KEY: METAL
<222> LOCATION: (5)..(10)
<223> OTHER INFORMATION: His6-tag
<220> FEATURE:
<221> NAME/KEY: DOMAIN
<222> LOCATION: (14)..(19)
<223> OTHER INFORMATION: Thrombin cleavage site
<220> FEATURE:
<221> NAME/KEY: DOMAIN
<222> LOCATION: (82)..(87)
<223> OTHER INFORMATION: GGGGSG linker

<400> SEQUENCE: 11

```
Met Gly Ser Ser His His His His His His Ser Ser Gly Leu Val Pro
1               5                   10                  15

Arg Gly Ser His Met Ser Asp Ser Asn Gln Gly Asn Asn Gln Gln Asn
                20                  25                  30

Tyr Gln Gln Tyr Ser Gln Asn Gly Asn Gln Gln Gln Gly Asn Asn Arg
            35                  40                  45

Tyr Gln Gly Tyr Gln Ala Tyr Asn Ala Gln Ala Gln Pro Ala Gly Gly
        50                  55                  60

Tyr Tyr Gln Asn Tyr Gln Gly Tyr Ser Gly Tyr Gln Gln Gly Gly Tyr
65                  70                  75                  80

Gln Gly Gly Gly Gly Ser Gly Val Asp Asn Lys Phe Asn Lys Glu Gln
                85                  90                  95

Gln Asn Ala Phe Tyr Glu Ile Leu His Leu Pro Asn Leu Asn Glu Glu
```

-continued

```
            100                 105                 110
Gln Arg Asn Ala Phe Ile Gln Ser Leu Lys Asp Asp Pro Ser Gln Ser
            115                 120                 125
Ala Asn Leu Leu Ala Glu Ala Lys Lys Leu Asn Asp Ala Gln Ala Pro
            130                 135                 140
Lys Val Asp Asn Lys Phe Asn Lys Glu Gln Gln Asn Ala Phe Tyr Glu
145                 150                 155                 160
Ile Leu His Leu Pro Asn Leu Asn Glu Glu Gln Arg Asn Ala Phe Ile
                165                 170                 175
Gln Ser Leu Lys Asp Asp Pro Ser Gln Ser Ala Asn Leu Leu Ala Glu
            180                 185                 190
Ala Lys Lys Leu Asn Asp Ala Gln Ala Pro Lys Ala Thr Gly Gly Gly
            195                 200                 205
Cys Ala Gly Cys Ala Gly Cys Cys Ala Thr Cys Ala Thr Cys Ala Thr
            210                 215                 220
Cys Ala Cys Cys Ala Thr Cys Ala Thr Ala Gly Cys Ala Gly Cys Gly
225                 230                 235                 240
Gly Thr Cys Thr Gly Gly Thr Thr Cys Cys Gly Cys Gly Thr Gly Gly
                245                 250                 255
Thr Ala Gly Cys Cys Ala Thr Ala Thr Gly Ala Gly Cys Gly Ala Thr
            260                 265                 270
Ala Gly Cys Ala Ala Thr Cys Ala Gly Gly Gly Thr Ala Ala Thr Ala
            275                 280                 285
Ala Thr Cys Ala Gly Cys Ala Gly Ala Ala Cys Thr Ala Thr Cys Ala
            290                 295                 300
Gly Cys Ala Gly Thr Ala Thr Ala Gly Cys Cys Ala Gly Ala Ala Thr
305                 310                 315                 320
Gly Gly Cys Ala Ala Thr Cys Ala Gly Cys Ala Gly Cys Ala Gly Gly
                325                 330                 335
Gly Cys Ala Ala Thr Ala Ala Thr Cys Gly Cys Thr Ala Thr Cys Ala
            340                 345                 350
Gly Gly Gly Thr Thr Ala Thr Cys Ala Gly Gly Cys Ala Thr Ala Thr
            355                 360                 365
Ala Ala Thr Gly Cys Ala Cys Ala Gly Gly Cys Ala Cys Ala Gly Cys
            370                 375                 380
Cys Thr Gly Cys Cys Gly Gly Thr Gly Gly Thr Thr Ala Thr Thr Ala
385                 390                 395                 400
Thr Cys Ala Gly Ala Ala Thr Thr Ala Thr Cys Ala Gly Gly Gly Cys
                405                 410                 415
Thr Ala Thr Thr Cys Thr Gly Gly Thr Thr Ala Thr Cys Ala Gly Cys
            420                 425                 430
Ala Gly Gly Gly Thr Gly Gly Ala Thr Ala Thr Cys Ala Gly Gly Gly
            435                 440                 445
Thr Gly Gly Thr Gly Gly Thr Gly Gly Ala Thr Cys Cys Gly Gly Thr
            450                 455                 460
Gly Thr Thr Gly Ala Thr Ala Ala Cys Ala Ala Thr Thr Thr Thr Ala
465                 470                 475                 480
Ala Cys Ala Ala Gly Ala Ala Ala Gly Cys Ala Gly Cys Ala Gly Ala
                485                 490                 495
Cys Gly Cys Cys Thr Thr Cys Thr Ala Cys Gly Ala Ala Ala Thr Thr
            500                 505                 510
Cys Thr Gly Cys Ala Thr Cys Thr Gly Cys Cys Gly Ala Ala Thr Cys
            515                 520                 525
```

-continued

Thr Gly Ala Ala Thr Gly Ala Ala Gly Ala Ala Cys Ala Gly Cys Gly
            530                 535                 540

Thr Ala Ala Thr Gly Cys Ala Thr Thr Thr Ala Thr Cys Cys Ala Gly
545                 550                 555                 560

Ala Gly Cys Cys Thr Gly Ala Ala Gly Ala Thr Gly Ala Thr Cys
            565                 570                 575

Cys Gly Ala Gly Cys Cys Ala Gly Ala Gly Cys Gly Cys Ala Ala
            580                 585                 590

Thr Cys Thr Gly Cys Thr Gly Gly Cys Cys Gly Ala Ala Gly Cys Ala
            595                 600                 605

Ala Ala Ala Ala Ala Ala Cys Thr Gly Ala Ala Thr Gly Ala Thr Gly
            610                 615                 620

Cys Cys Cys Ala Gly Gly Cys Ala Cys Gly Ala Ala Ala Gly Thr
625                 630                 635                 640

Gly Gly Ala Cys Ala Ala Thr Ala Ala Ala Thr Thr Cys Ala Ala Thr
            645                 650                 655

Ala Ala Ala Gly Ala Gly Cys Ala Cys Ala Ala Ala Ala Cys Gly
            660                 665                 670

Cys Gly Thr Thr Cys Thr Ala Thr Gly Ala Gly Ala Thr Cys Cys Thr
            675                 680                 685

Gly Cys Ala Thr Cys Thr Gly Cys Cys Thr Ala Ala Cys Cys Thr Gly
690                 695                 700

Ala Ala Cys Gly Ala Gly Gly Ala Ala Cys Ala Ala Cys Gly Cys Ala
705                 710                 715                 720

Ala Cys Gly Cys Cys Thr Thr Thr Ala Thr Thr Cys Ala Gly Thr Cys
            725                 730                 735

Ala Cys Thr Gly Ala Ala Ala Gly Ala Cys Gly Ala Cys Cys Cys Gly
            740                 745                 750

Thr Cys Ala Cys Ala Gly Thr Cys Ala Gly Cys Cys Ala Ala Cys Cys
            755                 760                 765

Thr Gly Cys Thr Gly Gly Cys Ala Gly Ala Gly Cys Cys Ala Ala
            770                 775                 780

Ala Ala Ala Ala Cys Thr Gly Ala Ala Cys Gly Ala Cys Gly Cys Ala
785                 790                 795                 800

Cys Ala Ala Gly Cys Thr Cys Cys Gly Ala Ala Ala Thr Ala Ala
            805                 810                 815

<210> SEQ ID NO 12
<211> LENGTH: 842
<212> TYPE: PRT
<213> ORGANISM: Artificial Sequence
<220> FEATURE:
<223> OTHER INFORMATION: Z Homodimer-GGGSG linker-Ure2(1-80)-His6
<220> FEATURE:
<221> NAME/KEY: DOMAIN
<222> LOCATION: (118)..(123)
<223> OTHER INFORMATION: GGGGSG linker
<220> FEATURE:
<221> NAME/KEY: METAL
<222> LOCATION: (205)..(210)
<223> OTHER INFORMATION: His6-tag

<400> SEQUENCE: 12

Met Val Asp Asn Lys Phe Asn Lys Glu Gln Gln Asn Ala Phe Tyr Glu
1               5                   10                  15

Ile Leu His Leu Pro Asn Leu Asn Glu Glu Gln Arg Asn Ala Phe Ile
            20                  25                  30

```
Gln Ser Leu Lys Asp Asp Pro Ser Gln Ser Ala Asn Leu Ala Glu
         35                  40                  45
Ala Lys Lys Leu Asn Asp Ala Gln Ala Pro Lys Val Asp Asn Lys Phe
 50                  55                  60
Asn Lys Glu Gln Gln Asn Ala Phe Tyr Glu Ile Leu His Leu Pro Asn
 65                  70                  75                  80
Leu Asn Glu Glu Gln Arg Asn Ala Phe Ile Gln Ser Leu Lys Asp Asp
                 85                  90                  95
Pro Ser Gln Ser Ala Asn Leu Leu Ala Glu Ala Lys Lys Leu Asn Asp
            100                 105                 110
Ala Gln Ala Pro Lys Gly Gly Gly Ser Gly Met Asn Asn Asn Gly
        115                 120                 125
Asn Gln Val Ser Asn Leu Ser Asn Ala Leu Arg Gln Val Asn Ile Gly
    130                 135                 140
Asn Arg Asn Ser Asn Thr Thr Thr Asp Gln Ser Asn Ile Asn Phe Glu
145                 150                 155                 160
Phe Ser Thr Gly Val Asn Asn Asn Asn Asn Ser Ser Ser Asn
                165                 170                 175
Asn Asn Asn Val Gln Asn Asn Ser Gly Arg Asn Gly Ser Gln Asn
            180                 185                 190
Asn Asp Asn Glu Asn Asn Ile Lys Asn Thr Leu Glu His His His
        195                 200                 205
His His Ala Thr Gly Gly Thr Thr Gly Ala Thr Ala Ala Cys Ala Ala
    210                 215                 220
Ala Thr Thr Thr Ala Ala Cys Ala Ala Ala Gly Ala Ala Cys Ala Gly
225                 230                 235                 240
Cys Ala Gly Ala Ala Cys Gly Cys Cys Thr Thr Cys Thr Ala Cys Gly
                245                 250                 255
Ala Ala Ala Thr Thr Cys Thr Gly Cys Ala Thr Cys Thr Gly Cys Cys
            260                 265                 270
Gly Ala Ala Thr Cys Thr Gly Ala Ala Thr Gly Ala Ala Gly Ala Ala
        275                 280                 285
Cys Ala Gly Cys Gly Thr Ala Ala Thr Gly Cys Ala Thr Thr Thr Ala
    290                 295                 300
Thr Cys Cys Ala Gly Ala Gly Cys Cys Thr Gly Ala Ala Ala Gly Ala
305                 310                 315                 320
Thr Gly Ala Thr Cys Cys Gly Ala Gly Cys Cys Ala Gly Ala Gly Cys
                325                 330                 335
Gly Cys Ala Ala Ala Thr Cys Thr Gly Cys Thr Gly Cys Cys Gly
            340                 345                 350
Ala Ala Gly Cys Ala Ala Ala Ala Ala Ala Cys Thr Gly Ala Ala
        355                 360                 365
Thr Gly Ala Thr Gly Cys Cys Cys Ala Gly Gly Cys Ala Cys Cys Gly
    370                 375                 380
Ala Ala Ala Gly Thr Gly Gly Ala Cys Ala Ala Thr Ala Ala Ala Thr
385                 390                 395                 400
Thr Cys Ala Ala Thr Ala Ala Ala Gly Ala Gly Cys Ala Ala Cys Ala
                405                 410                 415
Ala Ala Ala Cys Gly Cys Gly Thr Thr Cys Thr Ala Thr Gly Ala Gly
            420                 425                 430
Ala Thr Cys Cys Thr Gly Cys Ala Thr Cys Thr Gly Cys Cys Thr Ala
        435                 440                 445
Ala Cys Cys Thr Gly Ala Ala Cys Gly Ala Gly Gly Ala Ala Cys Ala
```

-continued

```
                450             455             460
Ala Cys Gly Cys Ala Ala Cys Gly Cys Cys Thr Thr Thr Ala Thr Thr
465                 470                 475                 480

Cys Ala Gly Thr Cys Ala Cys Thr Gly Ala Ala Gly Ala Cys Gly
                485                 490                 495

Ala Cys Cys Cys Gly Thr Cys Ala Cys Ala Gly Thr Cys Ala Gly Cys
                500                 505                 510

Cys Ala Ala Cys Cys Thr Gly Cys Thr Gly Gly Cys Ala Gly Ala Gly
                515                 520                 525

Gly Cys Cys Ala Ala Ala Ala Ala Cys Thr Gly Ala Ala Cys Ala Gly
                530                 535                 540

Ala Cys Gly Cys Ala Cys Ala Ala Gly Cys Thr Cys Cys Gly Ala Ala
545                 550                 555                 560

Ala Gly Gly Thr Gly Gly Thr Gly Gly Thr Gly Gly Ala Thr Cys Cys
                565                 570                 575

Gly Gly Thr Ala Thr Gly Ala Ala Thr Ala Ala Thr Ala Ala Cys Gly
                580                 585                 590

Gly Cys Ala Ala Cys Cys Ala Gly Gly Thr Gly Thr Cys Ala Ala Ala
                595                 600                 605

Cys Thr Thr Gly Thr Cys Ala Ala Ala Thr Gly Cys Thr Thr Ala
                610                 615                 620

Cys Gly Cys Cys Ala Gly Gly Thr Cys Ala Ala Thr Ala Thr Cys Gly
625                 630                 635                 640

Gly Cys Ala Ala Thr Ala Gly Ala Ala Ala Cys Thr Cys Cys Ala Ala
                645                 650                 655

Thr Ala Cys Thr Ala Cys Cys Ala Cys Ala Gly Ala Thr Cys Ala Gly
                660                 665                 670

Ala Gly Thr Ala Ala Cys Ala Thr Cys Ala Ala Cys Thr Thr Cys Gly
                675                 680                 685

Ala Ala Thr Thr Cys Thr Cys Cys Ala Cys Gly Gly Gly Thr Gly Thr
                690                 695                 700

Thr Ala Ala Thr Ala Ala Thr Ala Ala Thr Ala Ala Cys Ala Ala Cys
705                 710                 715                 720

Ala Ala Cys Ala Ala Thr Thr Cys Thr Thr Cys Ala Ala Gly Cys Ala
                725                 730                 735

Ala Cys Ala Ala Cys Ala Ala Cys Ala Ala Cys Gly Thr Gly Cys Ala
                740                 745                 750

Ala Ala Ala Cys Ala Ala Cys Ala Ala Cys Thr Cys Gly Gly Gly Thr
                755                 760                 765

Cys Gly Thr Ala Ala Thr Gly Gly Cys Thr Cys Thr Cys Ala Gly Ala
                770                 775                 780

Ala Cys Ala Ala Cys Gly Ala Thr Ala Ala Cys Gly Ala Ala Ala Ala
                785                 790                 795                 800

Cys Ala Ala Cys Ala Thr Cys Ala Ala Gly Ala Ala Cys Ala Cys Ala
                805                 810                 815

Cys Thr Cys Gly Ala Gly Cys Ala Cys Cys Ala Cys Cys Ala Cys Cys
                820                 825                 830

Ala Cys Cys Ala Cys Cys Ala Cys Thr Gly
                835                 840
```

ANTIBODY BINDING NANOFIBRILS

The Sequence Listing submitted herewith, entitled "Nov-13-2018-Sequence-Listing ST25.txt", created Nov. 13, 2018 and having a size of 24,484 bytes, is incorporated herein by reference.

TECHNICAL FIELD

The present embodiments generally relate to nanofibrils, and in particular to antibody binding nanofibrils.

BACKGROUND

The realization that properties of materials are altered substantially on a sub-μm scale has triggered the advent of nanotechnology. For instance, fibers or fibrils that have a diameter of less than 100 nm outperform their macroscopic counterpart with respect to surface area over volume ratio, variety of functionalities and mechanical characteristics. Nanofibrils can be synthetized from a large variety of materials, such as carbon, acrylonitrile, silicon, or from molecules of biological origins, such as cellulose, chitin and proteins.

The nature of protein assembly (fibrillation) into well-ordered nanofibrils or nanofibers is very intricate. Therefore, substantial effort has been made to elucidate the details of the fibrillation kinetics and to understand the molecular structure of nanofibrils. These studies are intended to provide insight into imperative aspects of life science that cover the building of functional aggregates and amyloid disease propagation. The mature fibrils possess a cross-β type structure, which is extremely rigid and exhibits extraordinary physical and chemical stability. This fact makes cross-β-fibrils a target for exploring all kinds of biotechnological applications. In this context, another useful property is that protein refolding and nanofibril assembly is self-propagating, which eliminates the need for continuous control of the aggregation, sometimes denoted polymerization. Moreover, since protein engineering is implemented on a genetic level, the fibrillating peptides can be adapted depending on the intended purpose of the nanofibril material.

The growing need for antibodies used for diagnostic purposes and medical treatment demands cost efficient means for their purification. Typically, antibodies are purified by ways of affinity chromatography based on a matrix of cross-linked agarose beads, which are covered with protein A, as for instance protein A SEPHAROSE® CL4B (GE Healthcare). Although protein A SEPHAROSE® is the workhorse for antibody purification, the immunoglobulin G (IgG) binding capacity of 20-50 mg/ml in connection with the high cost of the medium is a purification rate-limiting factor. The constraints posed by this purification protocol have promoted the development of alternative chromatographic methods based on the precise biochemical characteristics of IgG in order to circumvent the necessity of employing protein A. Another approach with the aim to increase the binding capacity is to alter the matrix for protein A display. For instance, it was demonstrated that polyester beads PolyBind-Z™ (PolyBatics Ltd.) yielded a binding capacity of 100 mg per g of drained medium.

Bifunctional protein nanofibrils were produced using seeding-induced self-assembling Sup35 protein from *Saccharomyces cerevisae* that is genetically fused with protein G or methyl parathion hydrolase (MPH) [1]. The protein G was capable of binding to IgG molecules and was used to anchor the nanofibrils onto a plate having immobilized antigens to which the IgG molecules had specificity. The immunoassay resulted in a 100-fold enhancement of the sensitivity when applied in the detection of the *Yersinia pestis* F1 antigen as compared to conventional enzyme-linked immunosorbent assay (ELISA).

Protein nanofibrils were produced using Sup35 proteins and human La proteins [26]. These protein nanofibrils were used to detect anti-SSB/La antibodies by binding to a fragment (a.a. 179-364) of the human La protein. Accordingly, the protein nanofibrils can be used to detect markers for Sjögren's syndrome.

However, there is a need for a technology having high binding capacity for antibodies and that can be used to capture and/or purify antibodies.

SUMMARY

It is an objective to provide antibody binding nanofibrils.

It is particular objective to provide such nanofibrils with improved antibody binding capacity.

These and other objectives are met by embodiments as disclosed herein.

An aspect of the embodiments relates to an antibody binding nanofibril obtainable by co-fibrillation of carrier proteins and carrier-Z fusion proteins at a molar ratio selected within an interval of from 1:0.20 to 1:0.90.

Another aspect of the embodiments relates to a kit for detecting presence of a chemical substance in a sample. The kit comprises antibody binding nanofibrils according to above and antibodies that specifically bind to the chemical substance in the sample. The carrier-Z fusion proteins of the antibody binding nanofibrils are capable of binding the antibodies.

A further aspect of the embodiments relates to an antibody capturing device comprising antibody binding nanofibrils according to above immobilized onto a solid surface.

Yet another aspect of the embodiments relates to a method of producing an antibody binding nanofibril. The method comprises co-fibrillating carrier proteins and carrier-Z fusion proteins at a molar ratio selected within an interval of from 1:0.20 to 1:0.90 to form the antibody binding nanofibril.

The antibody binding nanofibrils of the embodiments have improved antibody binding capacity. This improved antibody binding capacity is almost 20-fold higher as compared to protein A SEPHAROSE® affinity medium, which today is the golden standard with regard to antibody purification.

BRIEF DESCRIPTION OF THE DRAWINGS

The embodiments, together with further objects and advantages thereof, may best be understood by making reference to the following description taken together with the accompanying drawings, in which:

FIG. 1 schematically represents un-functional and functional Sup35 and Ure2 protein constructs employed in the examples. The abbreviation TS refers to thrombin cleavage site.

FIG. 2 illustrates Biacore sensorgrams of the interaction of human IgG with immobilized Sup35(1-61)-ZZ (A, E), ZZ-Ure2(1-80) (B), Sup35(1-61)-ZZ fibrils (C), ZZ-Ure2(1-80) fibrils (D) or Z (F). The proteins and fibrils were immobilized on a NTA-chip via a Hiss-tag. (A) Ligand: Sup35(1-61)-ZZ, Analyte: human IgG 5-40 nM (Thermo Scientific); (B) Ligand: ZZ-Ure2(1-80), Analyte: human IgG 5-40 nM; (C) Ligand: Sup35(1-61)-ZZ fibril (molar ratio of functional over un-functional protein 1:0.04), Analyte: human IgG 5-40 nM; (D) Ligand: ZZ-Ure2(1-80) fibril (molar ratio of un-functional over functional protein 1:0.04), Analyte: human IgG 5-40 nM; (E) Ligand: Sup35(1-61)-ZZ, Analyte: human IgG 5-40 nM (lab-purified); (F) Ligand: Z, Analyte: human IgG 5-40 nM. The original data is represented by points from low (solid fill) to high (no fill) concentration. The data was fitted to the 1:1 binding model (A, B, E, F) or the bivalent analyte model (C, D) indicated by solid lines.

Figure 3:
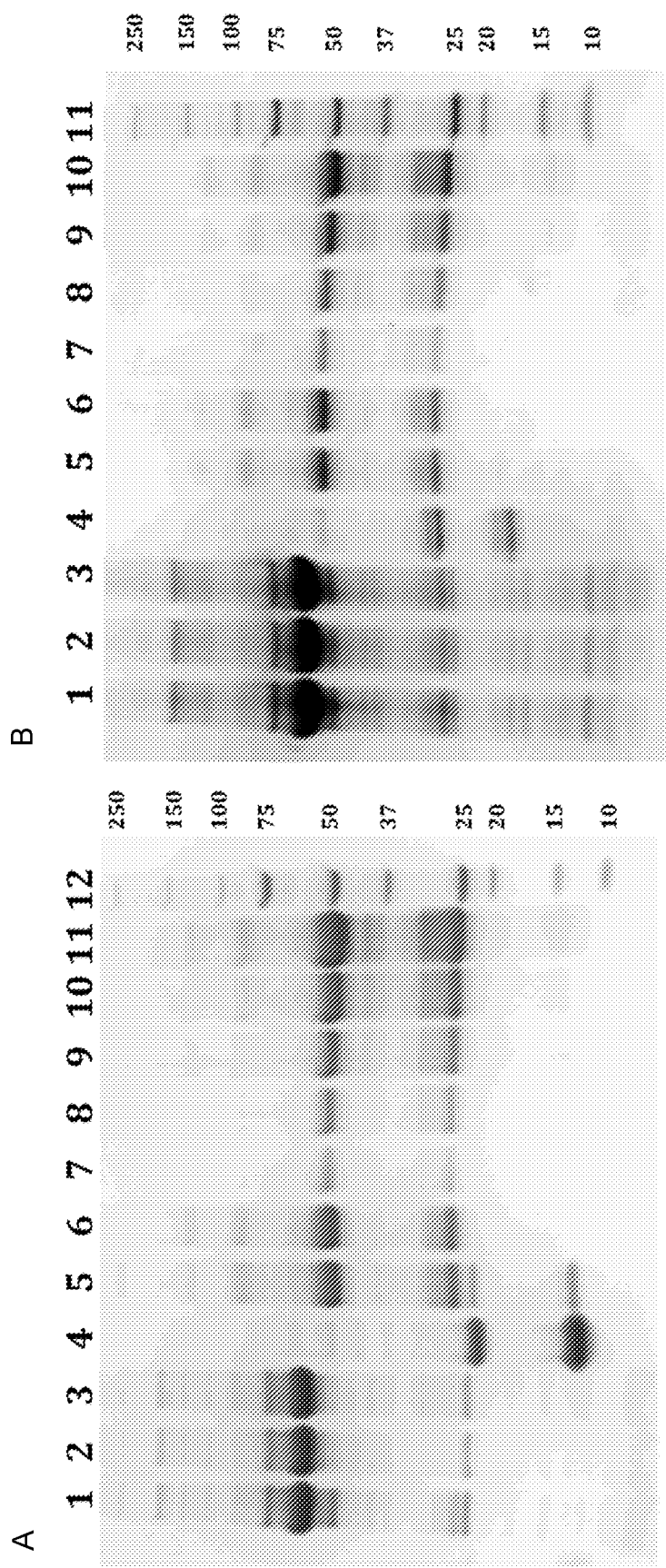

FIG. 3 illustrates purification of IgG from human serum using Sup35(1-60) (A) or Ure2(1-80) (B) nanofibrils that display the functional domain ZZ. (A) The heavy chain of human IgG is seen at 50 kDa, the light chain at 25 kDa, Sup35(1-61)-ZZ at 22 kDa and Sup35(1-61) is visible at 14 kDa. Lane 1. Human Serum; 2. Supernatant after centrifugation and incubation with the fibrils; 3. Wash; 4. Insoluble material remaining after elution; 5. Eluate; 6. Eluate after gel-filtration; 7.-11. Human IgG 0.0625-1 mg/ml (Thermo Scientific); 12. Precision Plus Protein Unstained Standards (Biorad). (B) The heavy chain of human IgG is seen at 50 kDa, the light chain at 25 kDa, ZZ-Ure2(1-80) at 25 kDa and Ure2(1-80) is visible at 18 kDa. Lane 1. Human Serum; 2. Supernatant after centrifugation and incubation with the fibrils; 3. Wash; 4. Insoluble material remaining after elution; 5. Eluate; 6. Eluate after gel-filtration; 7.-10. Human IgG 0.125-1 mg/ml (Thermo Scientific); 11. Precision Plus Protein Unstained Standards (Biorad).

Figure 4A:
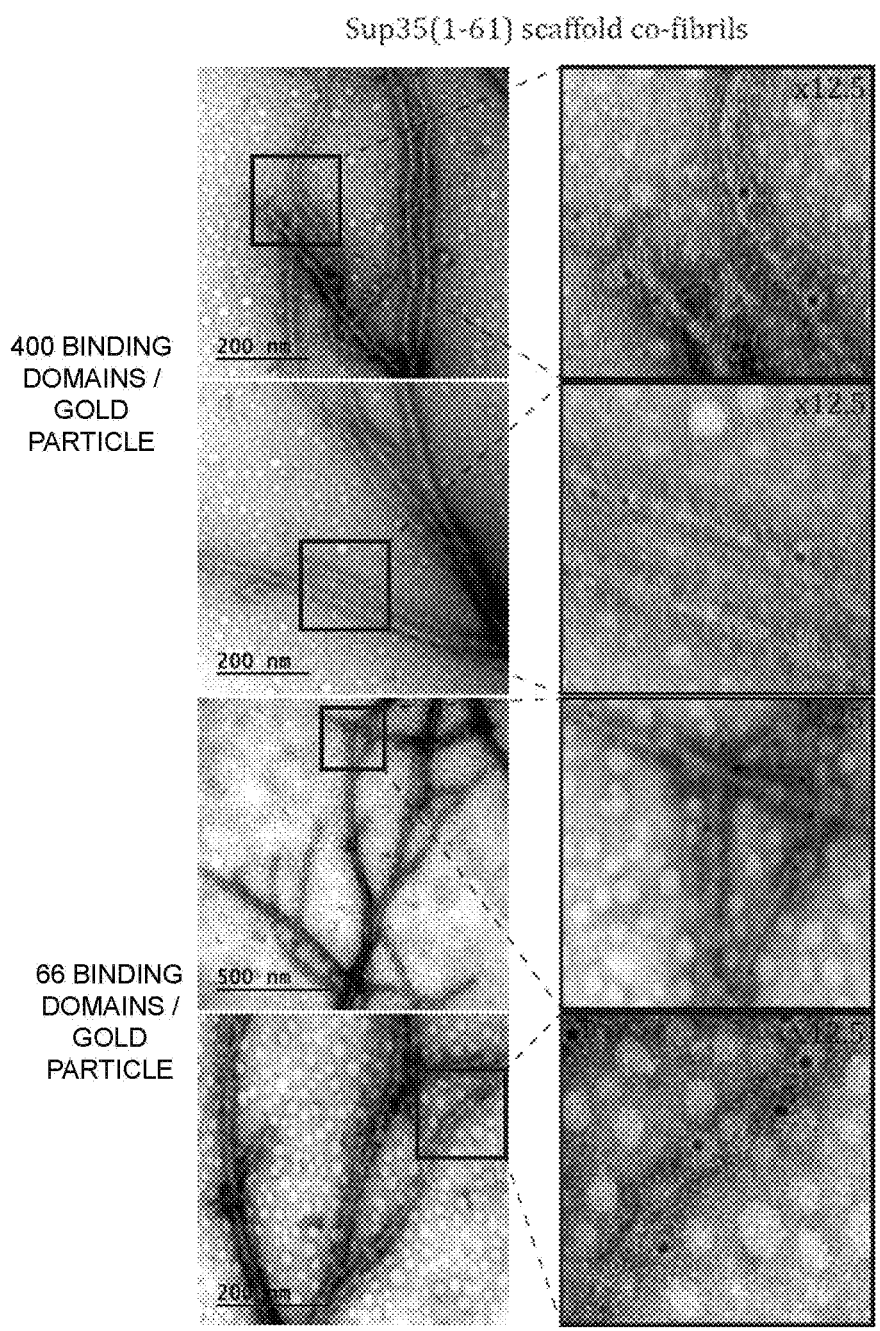
Figure 4B:
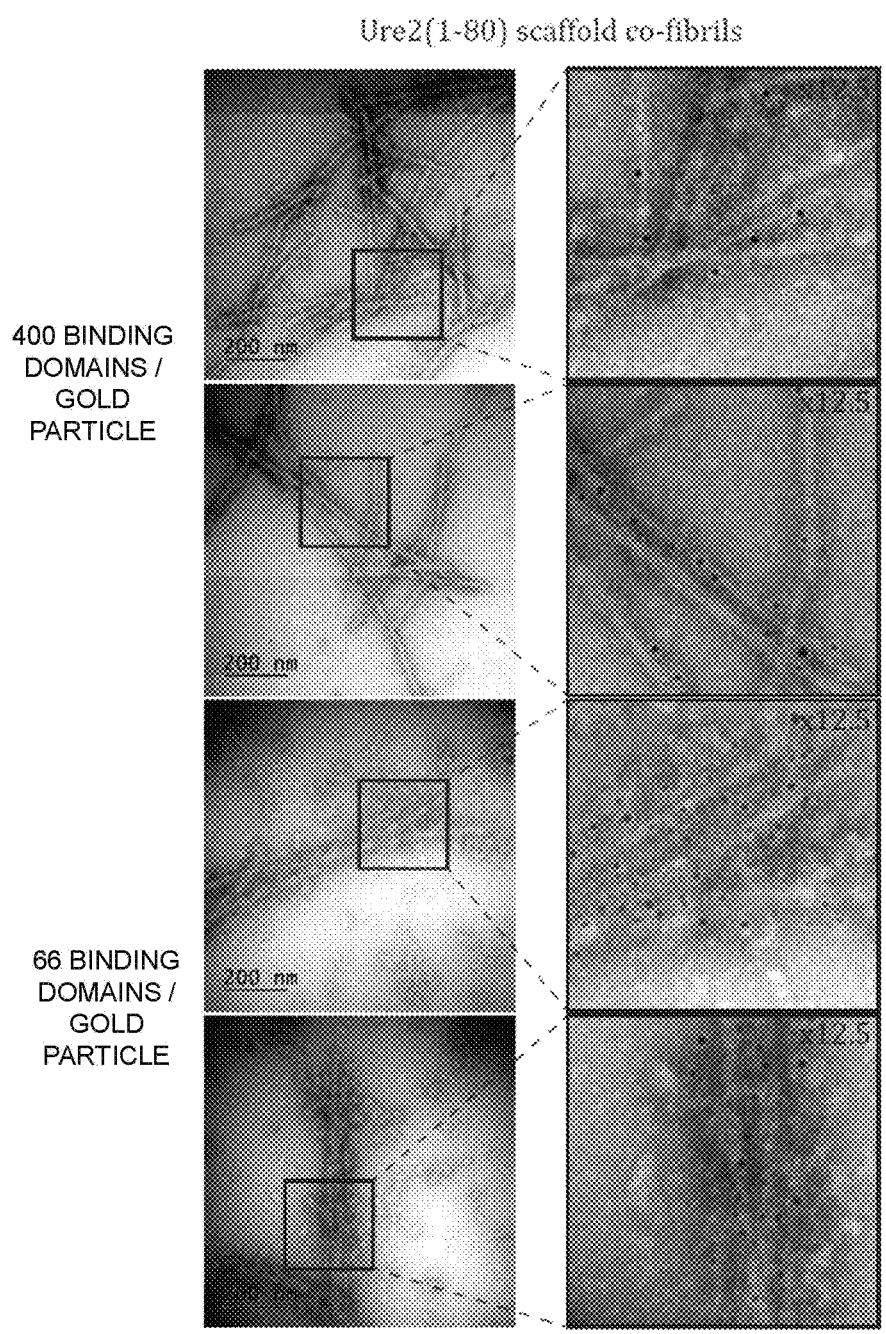

FIG. 4 illustrates transmission electron microscopy (TEM) images of antibody binding fibrils with a ratio of un-functional to functional protein of 1:0.16. The fibrils were saturated with human IgG and labeled with gold-conjugated secondary antibody. Indicated sections of the images were enlarged 12.5-25 fold. The black dots represent the 5 nm gold particles.

Figures 5A, 5B:
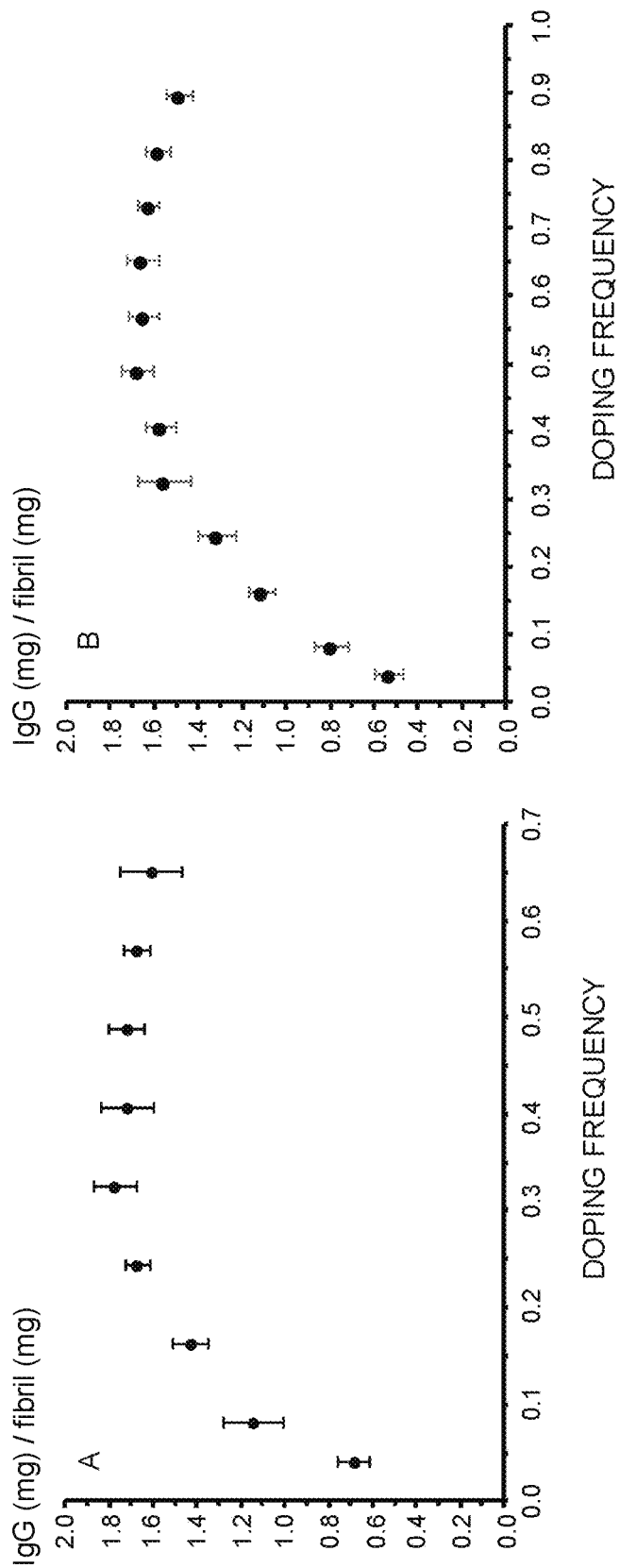
Figures 5C, 5D:
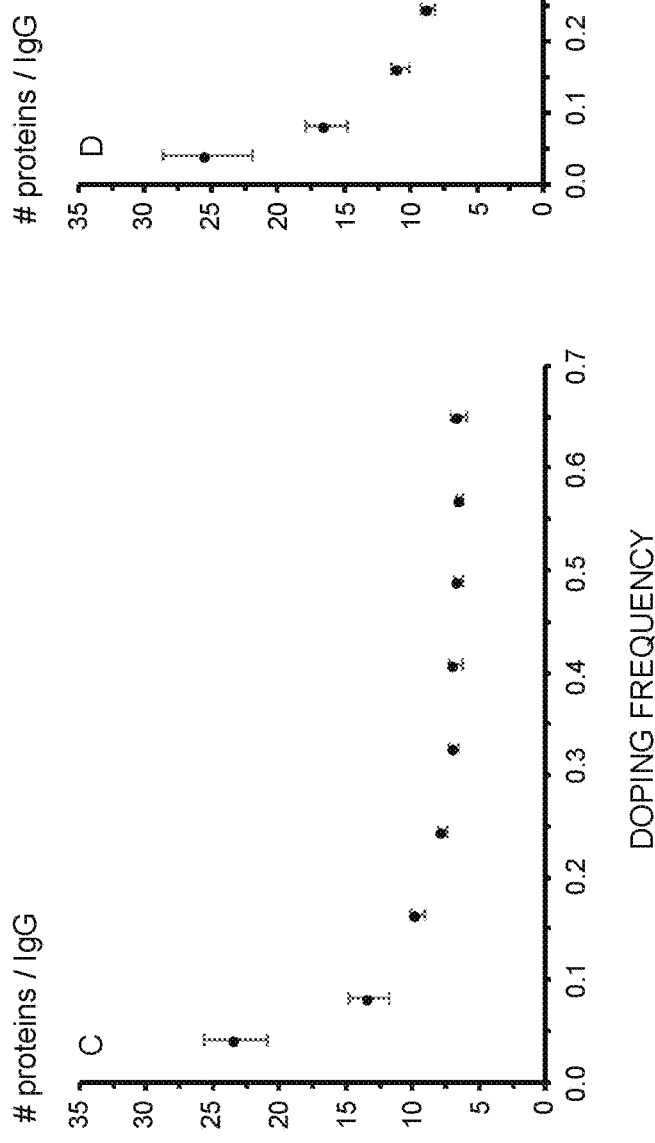
Figures 5E, 5F:
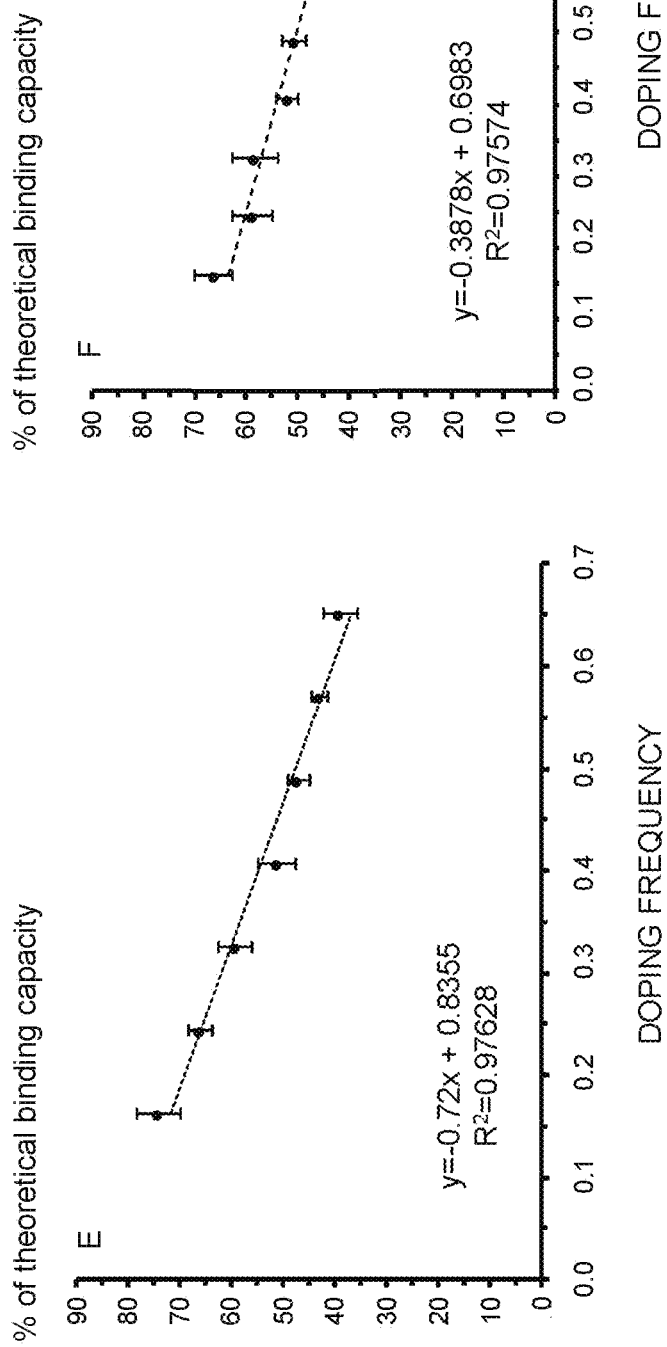

FIG. 5 schematically illustrates the influence of the co-fibril composition, i.e., the fibril doping frequency, on the IgG binding parameters. Several fibril types were studied, covering a molar ratio of 1:0.04-0.65 (Sup35 co-fibrils, A, C, E) or 1:0.04-0.9 (Ure2 co-fibrils, B, D, F) with respect to un-functional over functional protein. The molar frequency of the fusion protein relative to the scaffold protein is referred to as "doping frequency" on the x-axis. (A, B) IgG binding capacity of the co-fibrils as a function of the doping frequency. A local maximum of 1.8 mg (Sup35) and 1.7 mg (Ure2) IgG per mg fibril is reached at a molar ratio of 1:0.33 and 1:0.49 respectively. (C, D) The number of proteins required in order to bind one antibody molecule. (E, F) The experimentally determined IgG binding capacity divided by the theoretical maximal binding capacity shows a linear decrease if the fibrils with the lowest doping frequency, i.e., 0.04 and 0.08 are not considered. All data points represent average values from six independent measurements.

FIG. 6 is a flow chart illustrating a method of producing an antibody binding nanofibril according to an embodiment.

DETAILED DESCRIPTION

The present embodiments generally relate to nanofibrils, also referred to as nanofibers in the art. In particular, the embodiments relate to novel nanofibrils capable of binding antibodies, i.e., antibody binding nanofibrils.

The antibody binding nanofibrils of the embodiments are obtained by co-fibrillation, i.e., assembly, of two protein or peptide species, so called carrier proteins or peptides and functionalized carrier proteins or peptides. The carrier proteins are soluble protein monomers that aggregate into oligomers and further into fibrils and fibers in a molecular self-assembly process. This means that the carrier proteins, spontaneously or induced, aggregate and assemble into ever longer structures starting from a carrier protein monomer and growing into oligomers and further into fibrils. The fibrils generally have a diameter in the nanometer range and are, hence, denoted nanofibrils herein. Typical core diameters for nanofibrils are within 3 to 20 nm, dependent, among others, on the particular carrier proteins and the functional group(s) in the functionalized carrier proteins. The nanofibrils can, during the fibrillation process, grow into quite long fibrils of one or several micrometers in length. As a consequence of the minute diameter but comparatively large length of the nanofibers, the nanofibrils present a superior surface area to volume ratio.

The co-fibrillation of two protein species, i.e., the carrier proteins and the functionalized carrier proteins, implies that the resulting nanofibrils comprise functionalized groups, i.e., antibody binding groups or domains.

Bifunctional nanofibrils obtained by self-assembling of *Saccharomyces cerevisiae* Sup35 protein genetically fused with protein G and Sup35 protein genetically fused with MPH are known in the art [1]. The protein G groups of the nanofibrils bind to IgG molecules and were used to anchor the nanofibrils onto a plate having immobilized antigens to which the IgG molecules had specificity. Antibody binding nanofibrils were obtained by Sup35 protein genetically fused with a fragment of human La protein [26]. The prior art nanofibrils having antibody binding capability as exemplified in [1, 26] are, however, not optimized with regard to the antibody binding capacity of the nanofibrils.

The present embodiments are directed towards antibody binding nanofibrils with enhanced antibody binding capacity. This improved antibody binding capacity is achieved by using a selected interval of molar ratios between the carrier proteins and the functionalized carrier proteins. Experimental data as presented herein shows that the improvement in terms of antibody binding capability is only achieved for nanofibrils obtainable by co-fibrillation of the carrier proteins and the functionalized carrier proteins within the inventive molar ratio interval.

Thus, if the amount of functionalized carrier proteins is too low during the co-fibrillation process in relation to the amount of un-functional carrier proteins then the resulting antibody binding nanofibrils will have low number of antibody binding domains and thereby far from the maximum antibody binding capacity. However, if the amount of functionalized carrier proteins relative to the amount of un-functional carrier proteins increases above the upper end of the inventive molar range interval then the antibody binding capacity of the resulting nanofibrils drops. This unexpected reduction in antibody binding capacity as seen for nanofibrils with more functionalized domains might be due to decreased accessibility of the functionalized domains caused by steric restrictions within the nanofibrils. This finding was very surprising in the light of the prior art antibody binding nanofibrils [1, 26], in which each carrier protein was functionalized, i.e., either had an enzymatic domain (MPH) or an antibody binding domain (protein G or human La protein).

Thus, if the molar ratio of the carrier proteins and the functionalized carrier proteins is below the inventive interval then the nanofibril will present few antibody binding domains and thereby have far lower antibody binding capacity as compared to an antibody binding nanofibril of the embodiments. Correspondingly, if the molar ratio is instead above the inventive interval the nanofibril will present many antibody binding domains. However, due to steric restrictions the number of antibody binding domains that are actually accessible and that can bind antibodies will be lower as compared to an antibody binding nanofibril of the embodiments.

An aspect of the embodiments relates to an antibody binding nanofibril, i.e., nanofiber, obtainable by co-fibrillation of carrier proteins and carrier-Z fusion proteins at a molar ratio selected within an interval of from 1:0.20 to 1:0.90.

The antibody binding nanofibril is thereby obtainable by co-fibrillation, i.e., co-assembly or co-aggregation, of the carrier proteins and the functionalized carrier proteins, i.e., the carrier-Z fusion proteins, having antibody binding capability. The co-fibrillation implies that the two different species of monomers will aggregate into and form fibril structures, typically with a diameter within the nanometer range and typical lengths within the micrometer range. The selected molar ratio of the monomer species of the embodiments leads to formation of nanofibrils with a high antibody binding capacity with sufficiently large concentration of Z domains, i.e., antibody binding domains, but not too large concentration of such Z domains to reduce accessibility of the Z domains to antibodies.

The antibody binding nanofibril of the embodiments thereby comprises the carrier proteins and the carrier-Z fusion proteins at the molar ratio selected within the interval of from 1:0.20 to 1:0.90.

In an embodiment, the antibody binding domains of the antibody binding nanofibrils, i.e., the Z domains, are preferably distributed throughout the length of the antibody binding nanofibrils. Hence, in a preferred embodiment, the Z domains are not merely present in a portion of the antibody binding nanofibrils but are rather distributed, such as evenly distributed, throughout the whole length, or at least a major portion thereof, of the antibody binding nanofibrils.

Carrier-Z fusion protein as used herein indicates that a carrier protein monomer or domain, i.e., a fibrillating domain, is fused to at least one Z domain, i.e., antibody binding domain(s), to form a fusion protein. The fusion of the domains is preferably done at gene level, i.e., by combining or fusing a nucleotide sequence encoding the carrier protein with a nucleotide sequence encoding at least one Z domain. The fusion of the nucleotide sequences results in a gene encoding the carrier-Z fusion protein.

A currently preferred method of obtaining the carrier-Z fusion protein is production of the carrier-Z fusion protein in a host cell comprising an expression cassette, such as a plasmid, comprising the gene encoding the carrier-Z fusion protein under transcriptional control of a constitutive or inducible promoter, or comprising the gene encoding the carrier-Z fusion protein under transcriptional control of the promoter in the genome of the host cell. However, the embodiments are not limited thereto. Alternative methods of producing the carrier-Z fusion protein are possible, such as chemically connecting separately produced carrier proteins and Z domains.

In an embodiment, the N-terminal or the C-terminal of the carrier protein could be directly connected to the C-terminal or the N-terminal of the at least one Z domain in the carrier-Z fusion protein. Alternatively, the carrier protein and the at least one Z domain could be interconnected by a bridge or linker. Such a linker could be in the form of a short peptide of N amino acids. In an embodiment, N is preferably selected within an interval of from 3 to 15, preferably from 3 to 12, and more preferably from 3 to 7, such as about 5. In an embodiment, the amino acids of linker are preferably selected from glycine (G), alanine (A), threonine (T), serine (S), phenylalanine (F), glutamic acid (E) and lysine (K), and combinations thereof. An example of such a motif is A(EAAAK)$_n$A (SEQ ID NO: 1), wherein n is preferably 2-5, more preferably 2-3. Such a motif introduces a helix into the linker. Other helix forming motifs could be used for the linker. Further linkers that can be used according to the embodiments are disclosed in Table 3 in [2], the teaching of which with regard to linker motifs in Table 3 that could be used according to the embodiments is hereby incorporated by reference.

In an embodiment, the molar ratio between the carrier protein and the carrier-Z fusion protein is preferably within an interval of from 1:0.30 to 1:0.90 and more preferably within an interval of from 1:0.30 to 1:0.70. A particular preferred interval is from 1:0.30 to 1:0.50, see Tables 2 and 3 and FIGS. 5A and 5B.

These preferred and more limited molar ratio intervals result in nanofibrils with even higher antibody binding capacity as compared to the broader interval mentioned in the foregoing.

In an embodiment, the carrier proteins are Sup35 carrier proteins and the carrier-Z fusion proteins are Sup35-Z fusion proteins. In an embodiment, the Sup35 carrier protein comprises the complete amino acid sequence of *Saccharomyces cerevisiae* eukaryotic translation release factor Sup35, i.e., 685 amino acids. However, it is generally preferred to merely use a portion of the amino acid sequence, and then the fibrillating portion of the amino acid sequence. This fibrillating portion constitutes an N-terminal fragment of the Sup35 protein. Briefly, the Sup35 protein consists of three domains, the fibrillating N-terminal, which corresponds to amino acids 1 to 123, a middle domain (M-domain), which provides solubility to the Sup35 protein, and the C-terminal or domain that is essential for the native function of the Sup35 protein. Hence, in an embodiment, the Sup35 carrier proteins are N-terminal fragments of *S. cerevisiae* eukaryotic translation release factor Sup35 or, although generally less preferred, N+M-domain or domain fragments of *S. cerevisiae* eukaryotic translation release factor Sup35. The Sup35-Z fusion proteins are then fusion proteins of the N-terminal fragments of *S. cerevisiae* eukaryotic translation release factor Sup35 and at least one Z domain.

The N-terminal fragments thereby constitute a portion of the complete amino acid sequence of the Sup35 protein. In a particular embodiment, the N-terminal fragments consists of amino acids number 1 to 61 of *S. cerevisiae* eukaryotic translation release factor Sup35, denoted Sup35(1-61) herein. In another embodiment, the N-terminal fragment consists of amino acids number 1 to 47 of *S. cerevisiae* eukaryotic translation release factor Sup35. In a further embodiment, the N-terminal fragment consists of amino acids number 1 to 57 of *S. cerevisiae* eukaryotic translation release factor Sup35.

These N-terminal fragments of Sup35 adopt a β-sheet conformation during aggregation and can self-assemble in a fibrillation process into highly ordered cross-β structured nanofibrils [3, 4].

An antigen binding nanofibril obtainable by co-fibrillation, and preferably comprising, Sup35(1-61) proteins and Sup35(1-61)-Z fusion proteins has preferably a molar ratio of the Sup35(1-61) proteins and the Sup35(1-61)-Z fusion proteins within an interval of 1:0.30 to 1:40. The molar ratio is more preferably within an interval of from 1:0.30 to 1:0.35, such as preferably equal to about 1:0.33.

Experimental data as presented in Table 2 and FIG. 5A shows that the above mentioned intervals or value for the molar ratio are preferred with regard to using Sup35, and in particular Sup35(1-61) as the carrier protein.

The Sup35(1-61)-Z fusion protein preferably comprises, from its N-terminal towards its C-terminal, the Sup35(1-61) protein followed by at least one Z domain. In another embodiment, the order of the Sup35(1-61) protein and the at least one Z domain is switched. An optional bridge or linker may be present in the Sup35(1-61)-Z fusion protein interconnecting the Sup35(1-61) domain and at least one Z domain.

In another embodiment, the carrier proteins are Ure2 carrier proteins and the carrier-Z fusion proteins are Z-Ure2 fusion proteins. In an embodiment, the Ure2 carrier protein comprises the complete amino acid sequence of S. cerevisiae ureidosuccinate transport protein, i.e., 354 amino acids. However, it is generally preferred to merely use a portion of the amino acid sequence, and then the fibrillating portion of the amino acid sequence. This fibrillating portion constitutes an N-terminal fragment of the Ure2 protein. Hence, in an embodiment, the Ure2 carrier proteins are N-terminal fragments of S. cerevisiae eukaryotic ureidosuccinate transport protein. The Z-Ure2 fusion proteins are then fusion proteins of the N-terminal fragments of S. cerevisiae eukaryotic ureidosuccinate transport protein and at least one Z domain.

The N-terminal fragments thereby constitute a portion of the complete amino acid sequence of the Ure2 protein. In a particular embodiment, the N-terminal fragments consists of amino acids number 1 to 80 of S. cerevisiae ureidosuccinate transport protein, denoted Ure2(1-80) herein. Other particular embodiments involve using N-terminal fragments consisting of amino acids number 1 to 93, 1 to 65, 1 to 89 and 10 to 39 of S. cerevisiae ureidosuccinate transport Ure2.

These N-terminal fragments of Ure2 can self-assemble in a fibrillation process into highly ordered cross-β structured nanofibrils [5].

An antigen binding nanofibril obtainable by co-fibrillation, and preferably comprising, Ure2(1-80) proteins and Z-Ure2(1-80) fusion proteins preferably has a molar ratio of the Ure2(1-80) proteins and the Z-Ure2(1-80) fusion proteins within an interval of 1:0.45 to 1:55. The molar ratio is more preferably within an interval of from 1:0.47 to 1:0.51, such as preferably equal to about 1:0.49.

Experimental data as presented in Table 3 and FIG. 5B shows that the above mentioned intervals or value for the molar ratio are preferred with regard to using Ure2, and in particular Ure2(1-80) as the carrier protein.

The Z-Ure2(1-80) fusion protein preferably comprises, from its N-terminal towards its C-terminal, at least one Z domain followed by the Ure2(1-80) protein. In another embodiment, the order of the Ure2(1-80) protein and the at least one Z domain is switched. An optional bridge or linker may be present in the Z-Ure2(1-80) fusion protein interconnecting the Ure2(1-80) domain and the at least one Z domain.

Generally, the embodiments can use any order of the carrier protein and the at least one Z domain within the fusion protein, i.e., the carrier protein followed by, from N-terminal towards C-terminal, the at least one Z domain or the at least one Z domain followed by the carrier protein.

Sup35 and Ure2 are preferred carrier proteins for the antibody binding nanofibrils. The embodiments are, however, not limited thereto. This means that also other proteins or protein fragments capable of molecular self-assembly (MSA) could be used according to the embodiments and be functionalized with at least one Z domain. Non-limiting, but illustrative, examples of such other carrier proteins that can be used according to the embodiments include tandem repeat SH3 domain [6], B16 [7], bovine whey protein [8], b-tail peptide [9], alpha-synuclein [10], CsgA [11] and Rnq1 [12].

In an embodiment, the carrier-Z fusion proteins, such as Sup35(1-61)-Z fusion proteins or Z-Ure2(1-80) fusion proteins, are preferably fusion proteins between the carrier protein, such as Sup35(1-61) or Ure2(1-80), and an immunoglobulin G (IgG) binding domain of protein A, denoted Z domain herein.

Protein A is a 42 kDa surface protein originally found in the cell wall of the bacterium Staphylococcus aureus. It is encoded by the spa gene. It has found use in biochemical research because of its ability to bind immunoglobulins. It is composed of five homologous Ig-binding domains that fold into a three-helix bundle. Each domain is able to bind proteins from many mammalian species, most notably IgGs. It binds the heavy chain within the Fc region of most immunoglobulins and also within the Fab region in the case of the human VH3 family.

In an embodiment, the Z domain of the fusion protein could be any native or wild-type IgG binding domain of protein A, or a recombinant version of such an IgG binding domain of protein A. For instance, the Z domain could be an 8 kDa engineered B-domain variant of protein A [13]. This IgG binding domain is currently used as a scaffold to create AFFIBODY® molecules, and inherently binds the Fc portion of IgG with a dissociation constant ($K_D$) in the low nM range. Another example of Z domain that could be used according to the embodiments is the IgG binding domain used in MabSelect™. This IgG binding domain constitutes a Z domain in a recombinant protein A produced in Escherichia coli and specifically engineered to favor an oriented coupling that gives an enhanced binding capacity for IgG.

Other examples of IgG binding domains that could be used according to the embodiments include domains of protein G [14], protein A/G [15], protein M [16], protein L [17], SpA and Sbi [18] and protein H [19].

In a particular embodiment, the carrier-Z fusion proteins are carrier-Z dimer fusion proteins. Hence, in this embodiment, the carrier-Z fusion proteins preferably comprises two Z domains, i.e., a Z dimer (ZZ). Thus, preferred carrier-Z fusion proteins include Sup35(1-61)-ZZ and ZZ-Ure2(1-80).

The divalent Z, i.e., Z dimer (ZZ), is generally preferred over the monovalent Z-domain since it possesses a higher affinity to IgG, most likely due to avidity effects. The binding rate of ZZ to IgG is faster and the release of IgG is slower, see FIG. 2 and Table 1, which is potentially advantageous for applications that rely on complete occupation of the functional groups and reduced leakage.

The Z dimer is preferably in the form of two interconnected Z domains, i.e., ZZ. In an alternative embodiment, the Z dimer is in the form of two Z domains interconnected by a bridge or linker. For instance, the two Z domains could be interconnected by an inter-domain helix fragment (ZhZ) or by a flexible linker (ZfZ). An example of such inter-domain helix fragment is A(EAAAK)$_n$A (SEQ ID NO: 1), n is preferably 2-5. The flexible linker could be in the form of a peptide of M amino acids. In an embodiment, M is preferably selected within an interval of from 10 to 60, preferably from 15 to 50, and more preferably from 20 to 45. In an embodiment, the amino acids of linker are preferably selected from glycine (G), alanine (A), threonine (T), serine (S), phenylalanine (F), glutamic acid (E) and lysine (K), and combinations thereof. Further linkers that can be used according to the embodiments are disclosed in Table 3 in [2], the teaching of which with regard to linker motifs in Table 3 that could be used according to the embodiments is hereby incorporated by reference.

A linker could be used to confer the ability of binding both sides of the Fc fragment of IgG to the Z dimer, which would then in turn increase the affinity. Each Fc fragment possesses two Z binding sites that are separated by 69.6 Å. If the two Z domains in the Z dimer are interconnected without a linker then only one site is accessible. So the linker is preferably at least able to span a distance of 80 Å, considering that the linker is not completely extended. Generally, each amino acids gives 3.25 Å, so at least 25 amino acids are preferably used in the linker. Non-limiting examples of fully flexible linkers that could be used according to the embodiments include $(GGGGS)_{5-7}$ (SEQ ID NO: 2), $(GGGGT)_{5-7}$ (SEQ ID NO: 3), GSAGSAAGSGEF-GGGGS-GSAGS AAGSGEF (SEQ ID NO: 4), and GSAGSAAGSGEF-GGGGT-GSAGSAAGSGEF (SEQ ID NO: 5). Linkers or bridges that contain both a helix part and flexible pars include GGGGSGGGGS-A$(EAAAK)_{2-3}$A-GGGGSGGG GS (SEQ ID NO: 6), GGGGTGGGGT-A$(EAAAK)_{2-3}$A-GGGGTGGGGT (SEQ ID NO: 7), and GSAGSAAGSGEF-A$(EAAAK)_{2-3}$A-GSAGSAAGSGEF (SEQ ID NO: 8).

Although it is possible to interconnect the two Z domains with a helix fragment or a linker, experimental data indicate that such Z dimers, i.e., ZhZ and ZfZ, do not have any increased affinity for antibodies and IgG as compared a Z dimer consisting of two interconnected Z domains, i.e., ZZ.

The antibody binding nanofibrils of the embodiments are capable of binding antibodies with a high affinity and high capacity. The antibody binding nanofibrils are preferably capable of binding IgG antibodies.

In an embodiment, the antibody binding nanofibril has a binding capacity of at least 1.5 mg IgG per mg nanofibril. In a preferred embodiment, the antibody binding nanofibril has a binding capacity of at least 1.6 mg IgG per mg nanofibril, more preferably at least 1.7 mg IgG per mg nanofibril, such as at least 1.8 mg IgG per mg nanofibril.

Experimental data as presented herein shows that nanofibrils made by co-fibrillation of Ure2(1-80) and ZZ-Ure2 (1-80) can achieve a binding capacity of about 1.7 mg IgG per mg nanofibril, whereas nanofibrils made by co-fibrillation of Sup35(1-61) and Sup35(1-61)-ZZ can achieve a binding capacity of about 1.8 mg IgG per mg nanofibril. These binding capacities have been achieved even without any optimization of the binding conditions used when binding IgG molecules to the Z domains of the antibody binding nanofibrils.

However, even under these non-optimized binding conditions, the antibody binding nanofibrils of the embodiments have a binding capacity that is almost 20-fold more as compared to protein A SEPHAROSE® affinity medium, such as protein A SEPHAROSE® CL4B (GE Healthcare), which today is the golden standard with regard to antibody purification.

Another aspect of the embodiments relates to an antibody binding nanofibril according to the embodiments comprising at least one antibody bound to at least one Z domain of a carrier-Z fusion protein of the antibody binding nanofibril. In an embodiment, the at least one antibody is at least one IgG molecule.

FIG. 6 is a flow chart illustrating a method of producing an antibody binding nanofibril according to the embodiments. The method comprises co-fibrillating, in step S2, carrier proteins and carrier-Z fusion proteins at a molar ratio selected within an interval of from 1:0.20 to 1:0.90 to form the antibody binding nanofibril.

In various embodiments, the particular molar ratio intervals, carrier proteins and Z domains mentioned in the foregoing could be used in the method of FIG. 6.

In an optional embodiment, the method also comprises step S1. This step S1 comprises producing seeds by sonicating carrier proteins in an aqueous solution. The method then continues to step S2, which, in this embodiment, comprises incubating the seeds with the carrier proteins and the carrier-Z fusion proteins at the molar ratio to form the antibody binding nanofibril.

The seeds formed in step S1 thereby acts as seeds to which monomers of the carrier proteins and the carrier-Z fusion proteins can aggregate to growth the antibody binding nanofibrils.

The aqueous fibrillation buffer could be any aqueous buffer solution that preferably has a pH within an interval of from pH 7.0 to about 8.5, such as from about 7.0 to about 8.0. Non-limiting but illustrative examples of such aqueous buffer solutions include potassium phosphate (KPi) buffer or Tris-HCl buffer.

Preferred conditions for fibrillation include, but are not limited to, a temperature within the interval of from 0° C. to 42° C., a pH within the interval of from 3 to 9, a salt concentration of from 0 mM to 200 mM, a detergent concentration, such sodium dodecyl sulfate (SDS), of from 0 µM to 150 µM, a constant rotation speed of from 0 rpm to 600 rpm, and a fibrillation time of from a few hours to several days. A change in these conditions may influence fiber morphology and the completeness of aggregation. Also, fibrillation kinetics is to a large extent dependent upon the concentration of the carrier protein.

The antibody binding nanofibrils of the embodiments comprise and are made of the carrier proteins and the carrier-Z fusion proteins within the selected molar ratio interval. The functionalized domains of the antibody binding nanofibrils are then the Z domains having antibody binding capability. It is, though, possible to also introduce other functionalized domains in the antibody binding nanofibrils by including other carrier—functionalized domain fusion proteins during the co-fibrillation process. Non-limiting, but illustrative examples, of such other functionalized domains could be enzymes, metal binding domains, cytochrome p450, etc. However, such other functionalized domains could have a negative effect on the accessibility of antibodies to the Z domains of the antibody binding nanofibrils. Hence, it is generally preferred, at least in antibody purification applications, to use antibody binding nanofibrils without any functionalized domains besides the Z domains.

There is a steadily growing demand for antibodies, and in particular monoclonal antibodies, which are used as therapeutic agents and for diagnostic purposes. Hence, there is a growing need for high load antibody purification methods that are cost efficient. The current gold standard of antibody purification is affinity-chromatography using the highly selective medium protein A SEPHAROSE®. Nevertheless, the productivity of IgG purification is strained by the limited binding capacity of protein A SEPHAROSE®. To conquer the set boundaries, antibody binding nanofibrils could be employed as a scaffold for displaying the IgG binding Z-domain dimer. The superior surface area to volume ratio offered by the nanofibrils, is extremely suitable for such an antibody purification application.

Accordingly, the antibody binding nanofibrils of the embodiments can advantageously be used in antibodies and monoclonal antibodies purification applications.

A further aspect of the embodiments thereby relates to an antibody capturing device comprising antibody binding nanofibrils of the embodiments immobilized onto a solid surface.

The immobilization of antibody binding nanofibrils onto the solid surface can be achieved according to various embodiments. In an embodiment, at least some of the carrier proteins, at least some of the carrier-Z fusion proteins or at least some of the carrier proteins and the carrier-Z fusion proteins comprise a His tag, such as a $His_n$ tag, at the N-terminal and/or the C-terminal of the carrier proteins and/or the carrier-Z fusion proteins. In a particular embodiment, n is preferably at least 5 and more preferably at least 6, typically denoted polyhistadine tag in the art. An upper end of n is preferably 14. For instance, a Hiss tag could be connected to the N-terminal of the Sup35(1-61) and Ure(1-80) carrier proteins, to the N-terminal of the Sup(1-35)-ZZ fusion protein and/or to the C-terminal of the ZZ-Ure2(1-80) fusion protein, see FIG. 1.

Such a His tag enables the antibody binding proteins to be immobilized onto a $Ni^{2+}$ or $Co^{2+}$ charged surface. The surface could then be the surface of an affinity resin containing bound bivalent or cobalt ions. These resins are generally SEPHAROS® or agarose functionalized with a chelator, such as iminodiacetic acid (IDA) or nitrilotriacetic acid (NTA) for nickel and carboxylmethylaspartate (CMA) for cobalt. An example of such chelator functionalized resin is the HiTrap Chelating HP column (GE Healthcare). Further examples of solid surfaces that could be used to immobilize antibody binding nanofibrils through the interaction between His tags and $Ni^{2+}$ or $Co^{2+}$ are NTA, IDA or CMA chips or beads.

Also other immobilization solutions besides His tag—$Ni^{2+}/Co^{2+}$ are possible. For instance, biotin-streptavidin or biotin-avidin could be used to immobilize the antibody binding nanofibrils onto the solid surface. In such an approach, the N or C terminal of at least some of the carrier proteins and/or at least some of the carrier-Z fusion proteins are directly or indirectly connected to a biotin molecule or a streptavidin or avidin molecule. In such an approach, the solid surface comprises immobilized streptavidin or avidin molecules or biotin molecules.

Furthermore, there are numerous ways of coupling the nanofibrils covalently to a solid surface [20, 21]. For instance, hexamethylene, which serves as a spacer arm, reacts readily with the carbonyl groups of diamine poly (methylmethacrylate) (PMMA), better known under the trivial name acrylic glass. Carbodiimide may then be used to covalently link the carboxylic group of aspartic acid or glutamic acid to the spacer arm. Another option is the immobilization on epoxy resins. This is accomplished by activation of the hydroxyl groups of the resin with cyanuric acid, which in turn reacts with amine-groups, displayed by amino acids, such was lysine, asparagine and glutamine. Other surfaces that have been used previously for protein immobilization include, but are not limited to, PDMS derivatized with dextran, cellulose, gold and polystyrene, among others. However, these coupling techniques will result in unspecific attachment of the fibers.

Specific chemical coupling to a surface can be achieved by employing Sup35(1-61) or Ure2(1-80) displaying a C-terminal cysteine residue (Sup35(1-61)-Cys or Ure2(1-80)-Cys). Due to the absence of cysteine residues in the carrier proteins Sup35(1-61) or Ure2(1-80) and their functionalized counterparts, Sup35(1-61)-Cys and Ure2(1-80)-Cys can be added during the fibrillar assembly and, thus, be incorporated into the nanofibril. The introduction of only very few carrier proteins displaying cysteine ensures that coupling takes place at very few places along the nanofibril, preferentially one, conferring the ability of free horizontal movement upon the remaining nanofibril. In an optional embodiment, the N or C terminal of the carrier proteins and/or the carrier-Z fusion proteins does not necessarily have to be directly connected to the immobilization or anchoring tag or molecule. It is possible to have a linker or bridge between the N or C terminal and the immobilization or anchoring tag or molecule. In such an approach, the linker or bridge could be in the form of or comprise a restriction enzyme cleavage site, which is shown in FIG. 1 where the protease cleavage site is exemplified by a thrombin cleavage site (TS). This provides an efficient way of releasing the immobilized antibody binding nanofibrills from the surface by addition of the particular protease.

The detection of biomarkers indicative of an early stage of disease propagation is critical for successful treatment of the patient. Therefore, immunoassays are constantly improved, through optimization of the ELISA and the development of advanced variants thereof, with the aim to lower the limit of detection (LOD) and limit of quantification (LOQ) of disease specific proteins, which are released into the blood serum. Digital ELISA, i.e., the isolation of microbeads that capture proteins that are enzyme labeled into 50 fL reaction chambers, has lowered the limit of detection below the fM range, but requires advanced lab-equipment and trained personal. On the other hand, lateral flow immunoassays (LFA) are suited for point of care (POC) detection but fail to detect biomarkers below $10^{-11}$ M as they suffer from low antibody binding capacity of the membrane. However, identification of the frequently mentioned prostate cancer biomarker prostate-specific antigen (PSA), infectious diseases such as human immunodeficiency virus (HIV), neurological disorders and others typically require detection limits of $10^{-12}$ to $10^{-16}$ M. To overcome these restrictions, preconcentration of the target protein allows some improvement. Another option to lower the LOD of LFAs is to drastically increase the density of the capturing antibodies on the membrane. This could be achieved by employing antibody binding fibrils of the embodiments, which would amplify the available surface area, and thus increase the number of biomarker binding sites. Moreover, antibody binding nanofibrils have the potential to improve any immunoassay or device that would benefit from a larger surface area.

There is a need for highly sensitive assays for low concentration biomarkers, both for POC applications and laboratory diagnostics.

Hence, yet another aspect of the embodiments relates to a kit for detecting presence of a chemical substance in a sample. The kit comprises antibody binding nanofibrils according to the embodiments. The kit also comprises antibodies, such as IgGs, that specifically bind to the chemical substance in the sample. The carrier-Z fusion proteins of the antibody binding nanofibrils are capable of binding the antibodies.

The chemical substance could be any compound, agent, analyte or biomarker that can be recognized by antibodies, such as IgG, which are capable of binding to the Z domains of the antibody binding fibrils. Non-limiting, but illustrative examples, include biomarkers for cardiovascular diseases, such as troponin or high-sensitivity C-reactive protein (hsCRP); biomarkers for skull injury or trauma, such as S100 calcium-binding protein B (S100B), glial fibrillary acidic protein (GFAP), neurofilament light protein (NFL), D-dimer (a fibrin degradation product), brain natriuretic peptide (BNP); biomarkers for stroke, such as S100B, GFAP, NFL; biomarkers for various cancer types, such as PSA, nuclear matrix protein no. 22 (MP22), bladder tumor antigen (BTA), carcinoembryonic antigen (CEA), cancer antigen 15-3 (CA 15-3), cancer antigen 19-9 (CA 19-9); biomarkers for infectious diseases, such as biomarkers for influenza A or B, HIV; biomarkers for neurological diseases, such as Alzheimer's disease, Parkinson's disease, Multiple sclerosis, dementia, such as NFL, amyloid-β peptide, Tau.

Thus, the kit of the embodiments can be used to detect any chemical substance that is recognized by an antibody, preferably IgG molecule, which binds specifically to the chemical substance.

"Binds specifically" as used herein with regard to the binding of an antibody to a chemical substance, i.e., to an epitope of an antigenic chemical substance, is a term well understood in the art, and methods to determine such specific or preferential binding are also well known in the art. An antibody "specifically binds" to a chemical if it binds with greater affinity, avidity, more readily, and/or with greater duration than it binds to other chemical substances. Typically, binds specifically implies a dissociation constant ($K_D$)<1 µM, preferably <100 nM, and more preferably <10 nM.

It is of course possible to bind more than one type of antibodies to the antibody binding nanofibrils of the embodiments. In such a case, the two or more different antibody types may have specificity for and bind to different antigens, i.e., chemical substances, and/or different epitopes on a given antigen, i.e., chemical substance.

The sample containing the chemical substance, to which the antibody binds specifically, could be any sample, but is preferably a body sample from a human or animal body. Examples of illustrative such samples include body fluid samples, for instance a blood sample, a plasma sample or a serum sample. Other examples of body samples include tissue samples, cerebrospinal fluid samples, urine samples, etc.

The kit of the embodiments comprising the antibody binding nanofibrils as described herein thereby constitutes a valuable tool that can be used in POC and/or laboratory diagnostics, in which there is a need to detect presence of a particular chemical substance, and in particular such chemical substance that is present in a low concentration in a sample. The antibody binding nanofibrils of the embodiments designed to maximize or at least significantly improve the antibody binding capacity and having a superior surface area to volume ratio enable an extremely high amount or number of antibodies bound or attached to the antibody binding nanofibrils within a given volume or surface area, to which the antibody binding nanofibrils are immobilized.

For instance, as compared to traditional ELISA, such as sandwich ELISA, tests, in which capturing antibodies are attached to a solid surface, the present embodiments would instead attach the antibody binding nanofibrils to the solid surface, thereby significantly multiplying the number of capturing antibodies for a given area of the solid surface.

The kit of the embodiments can thereby be used to detect presence of chemical substances in a sample even at concentrations as low as pM, fM, aM or even lower.

EXAMPLES

In this study, nanofibrils intended for antibody purification, were designed with the aim to achieve a maximum binding capacity. To this end fibril weight was minimized by functionalization with the Z-domain (8 kDa), an engineered B-domain variant of protein A. The Z domain is used as a scaffold to create AFFIBODY® molecules, but inherently binds the Fc portion of IgG in the low nM range. In order to grant a maximal accessibility of the functional units and retained affinity, Sup35(1-61)-Z-dimer and Ure2(1-8)-Z-dimer fusion proteins were co-assembled with non-functional Sup35-fragments and Ure2-fragments, respectively. This strategy allowed us to optimize the fibril composition, which resulted in a concept material that exceeds the dynamic binding capacity of existing products by at least one order of magnitude.

Materials and Methods

Cloning

The genes of Sup35(1-61), Ure2(1-80), Sup35(1-61)-ZZ, ZZ-Ure2(1-80) and Z were codon optimized for expression in *Eshcerichia coli* and the DNA fragments were obtained from GeneArt Strings DNA Fragment synthesis (Thermo Scientific). The fragments were cleaved with FastDigest restriction enzymes (Thermo Scientific) and ligated into a pET28b(+) vector. The final constructs $His_6$-TS-Sup35(1-61) (SEQ ID NO: 9), $His_6$-TS-Ure2(1-80) (SEQ ID NO: 10), Hiss-TS-Sup35(1-61)-GGGSG linker-Z Homodimer (SEQ ID NO: 11), Z Homodimer-GGGSG linker-Ure2(1-80)-$His_6$ (SEQ ID NO: 12) and Hiss-Z (FIG. 1) were sequenced at the Uppsala Genome center (Science for Life Laboratory, Uppsala University, Uppsala, Sweden).

Expression and Purification

An overnight (ON) culture (Lysogeny-broth (LB) medium; 25° C.; 180 rpm) of transformed BL21star (DE3) carrying the pET28b(+) expression vector with the respective gene Sup35(1-61), Ure2(1-80), Sup35(1-61)-ZZ, or Z, was diluted 1:100 into 900 mL Terrific broth (TB) medium (30 µg/ml Kanamycin). The culture was grown at 37° C. and 180 rpm until $OD_{600}$ reached 0.6. Protein expression was induced by addition of isopropyl β-D-1-thiogalactopyranoside (IPTG) to a final concentration of 1 mM and the bacteria were additionally incubated for 4.5 h at 37° C. (Sup35(1-61), Ure2(1-80) and Z) or 5 h at 30° C. (Sup35(1-61)-ZZ) at 180 rpm. For expression of ZZ-Ure2(1-80) a starter-culture (TB-medium; 37° C.; 180 rpm; 5h) was diluted 1:180 into 900 mL TB-medium (30 µg/ml Kanamycin). The culture was grown for 180 rpm until $OD_{600}$ reached 1.0 at which point the culture was chilled on ice before addition of IPTG to a final concentration of 0.1 mM. Protein expression was carried out for 14 h at 20° C. and 180 rpm.

The cells were harvested at 3,500×g for 20 min at 4° C. in a Sorvall LYNX 6000 (Thermo Scientific) centrifuge using an F9-6x 1000 LEX rotor. The supernatant was discarded and the remaining cell pellet was re-suspended by gentle agitation in buffer LD [8 M urea, 20 mM Tris, 150 mM NaCl, pH 8] for Sup35(1-61) and Ure2(1-80) or buffer LN [25 mM Tris, 150 mM NaCl, pH 8] for Sup35(1-61)-ZZ, ZZ-Ure2(1-80) and Z and stored at −20° C. Cell lysis in native conditions was executed in a Cell Disruptor (Constant Systems) at 1.35 kba. Subsequently, 1,000 U of DNAse I (Boehringer Mannheim) and one Complete EDTA free protease inhibitor tablet (Roche) were added. After 30 min incubation on ice, the lysate was centrifuged in a Sorvall RC 6+ (Thermo Scientific) using an F21-8x50y rotor at 39,000×g and 4° C. for 30 min to remove any insoluble debris. Cell pellet re-suspensions in buffer containing urea were thawed and centrifuged in the same manner but for 60 min and at ambient temperature. Finally, the lysates were filtered through a syringe driven Filtropur S 0.45 µm filter (Sarstedt).

Protein purification was carried out on an Äkta Explorer platform at 4° C. for native buffer conditions or room temperature for denaturing conditions. In denaturing conditions, the $Ni^{2+}$ charged 5 ml HiTrap Chelating HP column (GE Healthcare) was equilibrated with buffer AD [8 M urea, 20 mM Tris, pH 8] before loading the cell lysate. Weakly binding proteins were first eluted with buffer AD containing 30 mM Imidazol. Sup35(1-61) was eluted at 90 mM Imidazol, giving rise to three successive peaks, whereas the $3^{rd}$ peak contained Sup35(1-61). Ure2(1-80) was eluted at 200 mM Imidazol. A 5 mL MonoQ column (Amersham Bioscience) was equilibrated with buffer AD, after which Sup35 (1-61) or Ure2(1-80) were loaded and pure protein was collected in the flow through. Sup35(1-61) was concentrated to >1,000 μM using a Vivaspin 20 MWCO 5,000 Da.

The functionalized Sup35(1-61)-ZZ, ZZ-Ure2(1-80) as well as Z were purified under native buffer conditions with buffer AN [25 mM Tris, pH 8]. The proteins were eluted essentially pure from the immobilized metal ion affinity chromatography (IMAC) column with the native buffer containing 200 mM Imidazol. As a final purification step, the proteins were loaded onto a HiLoad 16/600 Superdex 75 μg (GE Healthcare) gel filtration column. Purity and size of all proteins were confirmed by sodium dodecyl sulfate-polyacrylamide gel electrophoresis (SDS-PAGE) using 4-20% Mini-protean TGX Stain-Free Precast Gels (Biorad).

The absence of any post-translational modifications due to storage in 8 M urea was verified for Sup35(1-61) and Ure2(1-80) through matrix-assisted laser desorption/ionization (MALDI)—time of flight (TOF) mass spectroscopy (MS). Protein concentration of Sup35(1-61), Sup35(1-61)-ZZ, ZZ-Ure2(1-80), and Z was determined by measuring absorbance at 280 nm ($Abs_{280}$) and by using the calculated sequence specific extinction coefficient [22]. In addition, the bicinchoninic acid assay (Thermo Scientific assay kit) was used to determine the concentration of Ure2(1-80) and ZZ-Ure2(1-80). The proteins were aliquoted and flash frozen with liquid nitrogen before long term storage at −80° C.

Aggregation of Functionalized Nanofibrils

Co-fibrillation, that is simultaneous aggregation of Sup35 (1-61) with Sup35(1-61)-ZZ and Ure2(1-80) with ZZ-Ure2 (1-80), was implemented in buffer FBS [30 mM Tris-HCl, 200 mM NaCl, pH 8.0] and buffer FBU [10 mM KPi, 150 mM NaCl, pH 7.4] respectively. Functional Sup35(1-61) fibrils were assembled by first diluting 18 μg of Sup35(1-61) 50 times into buffer FBS. This sample was sonicated for 8 min in a Branson 2510 ultrasonication bath in a 1.5 mL Eppendorf vial. The seeds were then immediately added to a sample containing 79 μg Sup35(1-61) and 10-159 μg Sup35(1-61)-ZZ. Considering the amount of the seeds added, a final molar ratio of Sup35(1-61) to Sup35(1-61)-ZZ corresponding to 1:0.04-1:0.65 was obtained. In a likewise manner, to obtain Ure2(1-80) seeds the protein was concentrated with a Vivaspin 500 MWCO 3,000 Da at 9,000×g to approximately 1 mM and then diluted 50 times into buffer FBU. Next, 100 μg were sonicated (2 s on, 8 s off, 20% amplitude, total time 60 s) with a Vibra Cell VC 505 (Sonics) using a stepped microtip. The seeds were added immediately to a sample containing 71 μg Ure2(1-80) and 8-169 μg ZZ-Ure2(1-80), which yielded a final molar ratio of Ure2(1-80) to ZZ-Ure2(1-80) corresponding to 1:0.04-1:0.9, if the amount of seeds added is also considered. For complete aggregation the samples were incubated at room temperature overnight. The completeness of the fibrillation was tested through centrifugation to sediment the fibrils at 17,000×g for 10 minutes followed by measuring the absorbance at 280 nm of the supernatant with a Nanodrop1000 (Thermo Scientific) or SDS-PAGE to confirm the absence of any residual proteins. The assembled fibrils were stored at 4° C. until use.

Biomolecular Interactions

All interaction studies were executed using a surface plasmon resonance (SPR) assay on a Biacore X100 (GE healthcare) at 25° C. and a flow rate of 30 μL/min. The Hiss-tagged proteins were immobilized on an nickel ($Ni^{2+}$) chelated nitrilotriacetic (NTA) chip (GE Healthcare) by injecting 10 ng/ml Z for 30 s, ng/mL Sup35(1-61)-ZZ for 90 s or 160 ng/mL ZZ-Ure2(1-80) for 90 s over the nickel charged surface. Typically, a stable final immobilization level of 10 response units (RU) to 40 RU was reached. Polyclonal human IgG (Pierce) was prepared in a twofold dilution series in buffer HBS-P [10 mM HEPES, 150 mM NaCl, 3 mM EDTA, 0.05% TWEEN® 20, pH 7.4] and was varied between 5 to 40 nM. The analysis was implemented as a multiple cycle setup, i.e., complete regeneration of the $Ni^{2+}$ charged surface after each injection of analyte. The association phase was monitored for 180 s and the dissociation phase for 600 s. The data was fitted to a 1:1 binding model using the Biacore Evaluation software. Each experiment was performed as quadruplicates. A similar setup was used to record the binding kinetics of co-fibrils (molar ratio 1:0.04). The co-fibrils were diluted to 160 ng/ml (Sup35) or 1 μg/ml (Ure2) and injected over the nickel charged surface of the NTA-chip for 180 s which yielded an immobilization level of 30 RU. The concentration of the analyte (polyclonal IgG) was varied between 5 and 40 nM. The obtained sensorgrams were fitted to the bivalent analyte model.

Purification of IgG from Human Serum

Approximately 680 μg Sup35 co-fibrils with a molar ratio of 1:0.16 or 530 μg Ure2 fibrils with a molar ratio of 1:0.49 were washed two times with buffer FBS and incubated with human serum (3H Biomedical) at room temperature for 30 min. The fibrils were then sedimented through centrifugation at 17,000×g for 10 min in a Heraeus Pico17 Table Top centrifuge (Thermo Scientific) and washed rigorously three times. Bound IgG was eluted using buffer EB (0.1 M glycine-HCl, pH 3) and the total amount of eluted IgG was estimated through measuring absorbance at 280 nm. For polishing, the eluted IgG was loaded onto a Superdex 200 10/300 GL (GE Healthcare) using buffer AN. The successful purification of IgG was evaluated using SDS-PAGE.

Electron Microscopy

Polyclonal human IgG (Thermo Fisher Scientific) was used as a primary antibody to saturate the displayed ZZ-domains with a ratio equal to 1:0.16 fibrils. After incubation at room temperature for 30 min, secondary Goat Anti-Human IgG 5 nm gold conjugated (Sigma Aldrich) was added to the fibrils to a final ratio of 66 or 400 ZZ binding sites per immuno-gold particle. Through the additional weight, fibrils sedimented very quickly which allowed the removal of the supernatant and re-suspension in fresh buffer EM (5 mM Tris-HCl, pH 8). Washing was repeated four times using buffer EM. The fibrils were loaded onto a carbon-coated grid (SPI Supplies) and negative stained with 1% uranylacetat [23]. TEM images were taken at the SciLife lab BioVis facility (Rudbeck laboratory, Uppsala University, Uppsala, Sweden).

Binding Capacity of the Nanofibrils

The maximal IgG binding capacity of the co-fibrils displaying ZZ was determined as a function of the doping frequency. To this end co-fibrils were assembled with a relative molar ratio of unfunctional over functional fibril protein corresponding to 1:0.04-1:0.65 (Sup35) or 1:0.04-1:0.9 (Ure2). Depending on the ratio, 7.4-17.8 μg Sup35-scaffold co-fibrils or 6.6-17.8 μg Ure2-scaffold co-fibrils were incubated for 60 minutes at room temperature together with human IgG (Pierce). The amounts of antibodies added were in the range of 1.5-2 times the actual fibril binding capacity. Prior to use, the IgG was freshly diluted from stock and the final concentration was determined by measuring the absorbance at 280 nm ($\varepsilon\_percent=13.7$ g/100 ml$^{-1}$ cm$^{-1}$) in quadruplicates. Following incubation, the sample was centrifuged at 17,000×g for 10 min in a Heraeus Pico17 Table Top centrifuge (Thermo Scientific) and the absorbance at 280 nm of the supernatant was determined in triplicates. The absorbance at 280 nm of the supernatant was directly related to the amount IgG bound to the fibrils. The binding capacity of each fibril type was determined in sextuplicates.

Results

Protein Purification

Sup35(1-61) and Ure2(1-80) were purified in denaturing conditions, which yielded 10 mg and 20 mg protein per L of *E. coli* culture, respectively. MALDI-TOF MS confirmed the theoretical mass of Sup35(1-61) (8,995 Da) and Ure2(1-80) (10,793 Da), which implied the absence of any modifications due to storage in urea. The functional variants Sup35(1-61)-ZZ and ZZ-Ure2(1-80) were expressed and purified in native conditions. After IMAC purification the yield was estimated to 71 mg/L and 20 mg/L respectively. Likewise, purification of the Z domain yielded 89 mg/L pure protein after IMAC.

Biomolecular Interactions

Figure 2A:
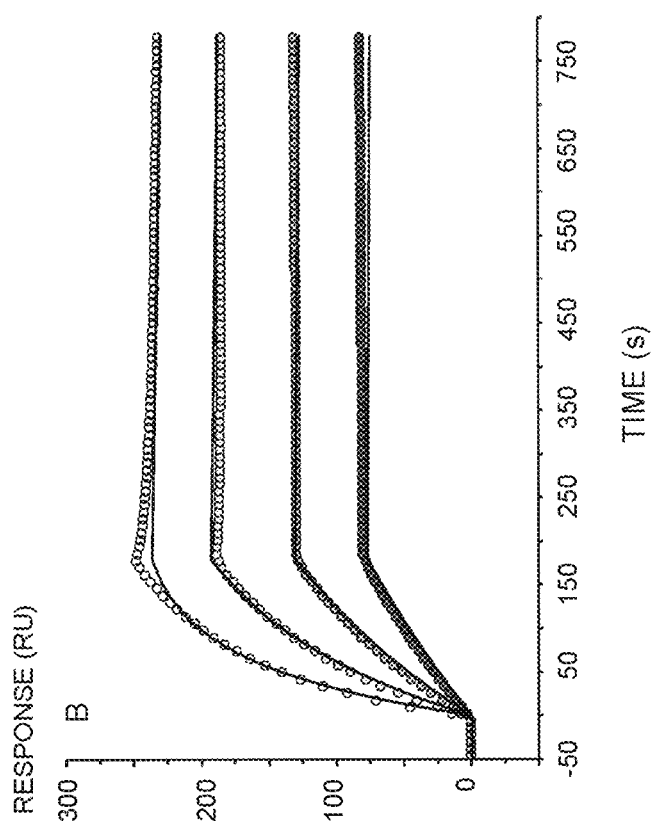
Figure 2B:
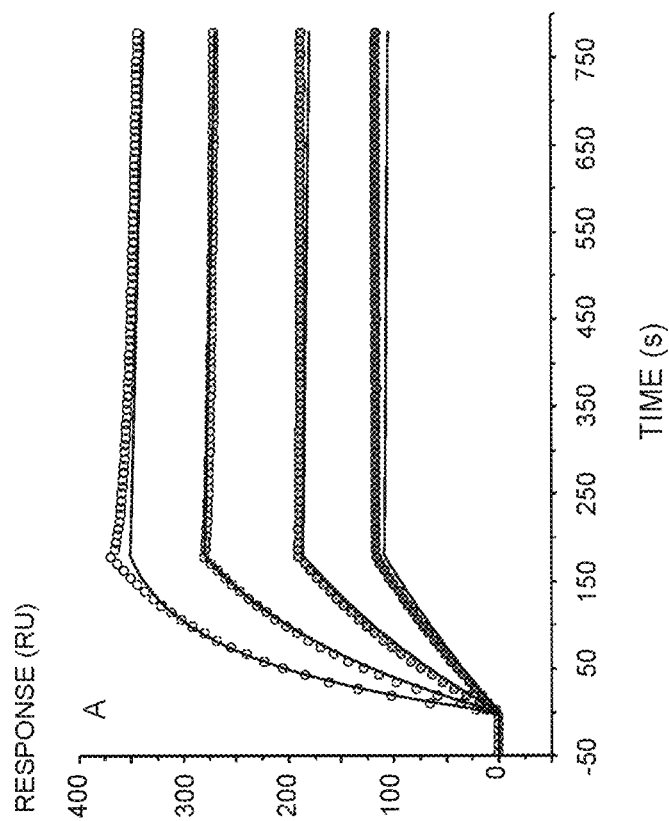

Designing nanofibrils with the aim to efficiently bind IgG is constitutively dependent upon the choice of the functional domain. The Z-domain is a carefully selected candidate for this purpose. Moreover, in previous studies it has been shown that the dimeric ZZ, provides increased binding affinity towards IgG compared to the individual Z domain [24]. Biacore was used to evaluate the retained potency of ZZ, utilized in the fusion protein Sup35(1-61)-ZZ and ZZ-Ure2(1-80) as an individual molecule and in the assembled fibril (FIGS. 2A and 2B). The results suggested (Table 1) that the kinetics were well in agreement with data available in the literature [24, 25]. However, $k_{off}$ is approximately one order of magnitude slower than previously reported values. A plausible justification for data dissimilarities is the fact that a Ni$^{2+}$-charged NTA-chip was utilized for protein immobilization via the Hiss-tag, to attain an optimal orientation of the functional ZZ. Contrary to this experimental design, previous data was obtained using unspecific immobilization through amine-coupling of IgG to a CM5 chip, which yielded a heterogeneous surface. Nevertheless, it can be concluded that ZZ was not impaired by its tag and that effective ZZ binding towards IgG remained intact which provides affinity in the high pM range.

TABLE 1

Association and dissociation constants of human IgG binding to the Z-domain present in different protein constructs

| Protein | $k_{on}$ (M$^{-1}$ s$^{-1}$ × 10$^5$) | $k_{off}$ (s$^{-1}$ × 10$^{-4}$) | $K_D$ (M × 10$^{-9}$) |
|---|---|---|---|
| Z[B] | 2.41 ± 0.31 | 3.42 ± 0.45 | 1.44 ± 0.27 |
| Sup35(1-61)-ZZ[B] | 3.82 ± 0.13 | 1.04 ± 0.32 | 0.27 ± 0.08 |
| Sup35(1-61)-ZZ fibril[A] | 3.22 ± 0.38 | 1.71 ± 0.38 | 0.62 ± 0.17 |
| ZZ-Ure2(1-80)[B] | 4.18 ± 0.17 | 0.74 ± 0.21 | 0.18 ± 0.05 |
| ZZ-Ure2(1-80) fibril[A] | 3.13 ± 0.24 | 1.18 ± 0.61 | 0.39 ± 0.21 |

[A]The data was fitted to a bivalent analyte model. The rates $k_{on}$ and $k_{off}$ are representative for the main component of the IgG - fiber interaction. The molar ratio of un-functional relative to functional protein in the co-fibrils were 1:0.04.
[B]The data was fitted to a 1:1 binding model.

Assembly and Functionality of the Co-Fibrils

The use of seeds to initiate the co-aggregation resulted in functional co-fibrils in less than one day, independent of the ratios of the two entities. Hence, the density of ZZ along the fibril was easily adjusted by variation of Sup35(1-61)-ZZ or ZZ-Ure2(1-80) concentration subsequent to the aggregation of the co-fibril. Successful fibrillation was evaluated by removing the fibrils from suspension through centrifugation. The complete absence of soluble proteins in the supernatant was confirmed by absorbance measurement or SDS-PAGE.

Figure 2C:
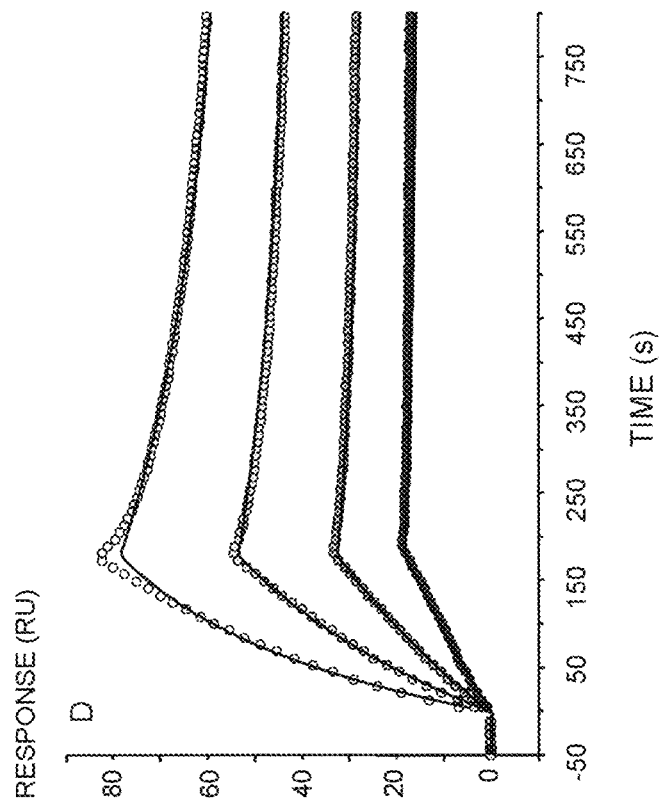
Figure 2D:
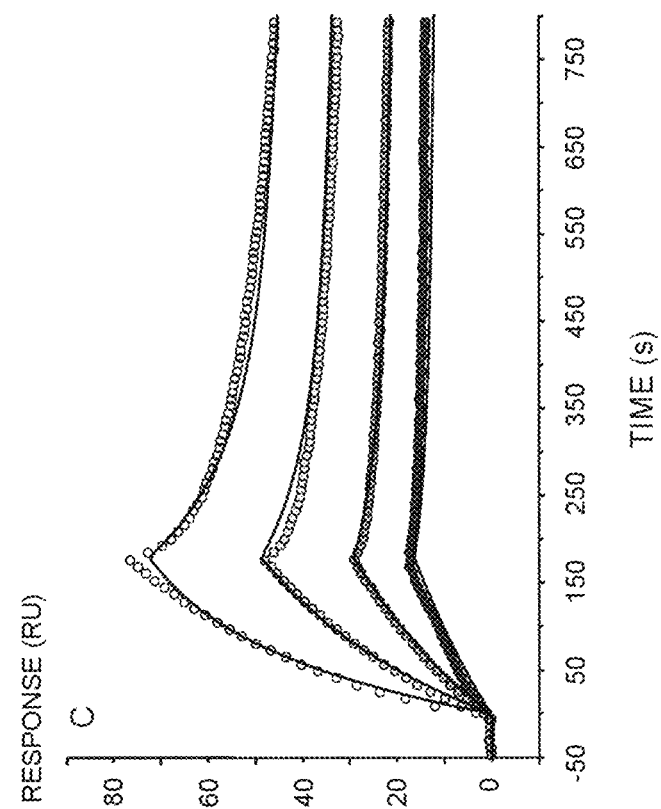
Figures 2E, 2F:
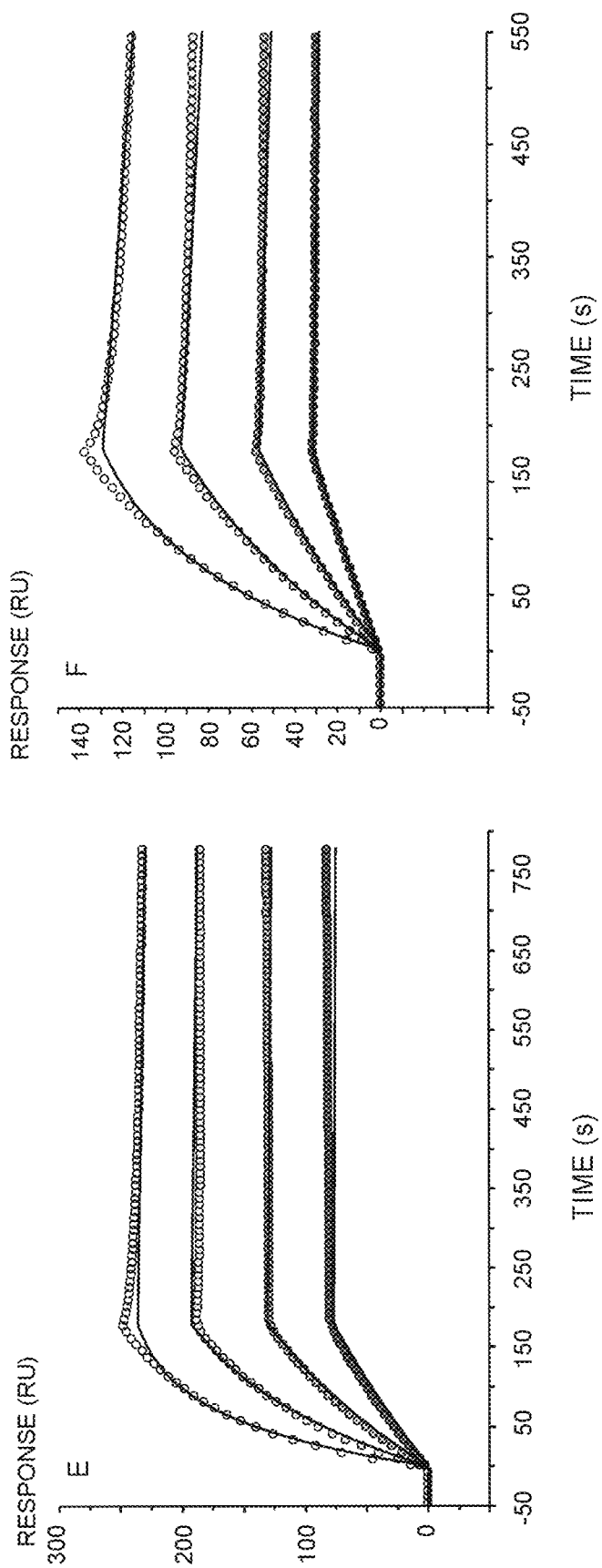

To assess the preserved functionality of ZZ displayed on the assembled material, once more the SPR technique was applied to measure the kinetic binding rates of IgG to the co-fibrils (FIGS. 2C and 2D). The sensorgrams of this interaction were more complex and could not be fitted to the 1:1 binding model. This observation agrees with the rationale, that co-fibril immobilization is not expected to offer equal accessibility of all binding sites. Consequently, the bivalent analyte model was used to fit data. The principal component of the interaction yielded rates that were consistent with data obtained from the soluble chimeric proteins and demonstrated the functionality of ZZ displayed on Sup35(1-61) as well as on Ure2(1-80) fibrils. To accentuate this finding, purification of IgG from a complex matrix was attempted. To this end, ZZ functionalized fibrils with doping frequency 1:0.16 and 1:0.49 for Sup35 and Ure2 scaffold co-fibrils, respectively, were incubated together with human serum. The fibrils were then pelleted by centrifugation, washed extensively, and stripped of IgG with 0.1 M Glycine-HCl, pH 3. The SDS-PAGE analysis of the purification showed that the functional material exclusively bound IgG and did not bind other highly abundant proteins (FIGS. 3A and 3B). Purity of the eluted antibodies was comparable to the commercially obtained IgG, with the exception of the presence of presumably small fibril fragments that were not removed by centrifugation. To increase purity and remove the small fibril fragments, the sample was gel filtrated. In total 720 µg (Sup35-scaffold co-fibrils) and 650 µg (Ure2-scaffold co-fibrils) IgG were purified from human serum, which corresponded to a yield of 1.06 and 1.22 mg IgG/mg fibril, respectively. The integrity of the purified antibodies was verified by repeating the SPR-assay initially performed with commercially obtained pure IgG. The lab-purified IgG interaction with immobilized Sup35(1-61)-ZZ yielded binding constants ($k_{on}$ 3.30±0.24×10$^5$M$^{-1}$ s$^{-1}$, $k_{off}$ 0.82±0.41× 10$^{-4}$ s$^{-1}$ and $K_D$ 0.25±0.12 nM) that are in fact identical with the rates listed in (Table 1).

The functionality of the co-fibrils was also verified using TEM (FIG. 4). The fibrils were first completely saturated with human IgG and then labeled with gold conjugated secondary antibody. Evidently, the gold labeled antibodies were evenly distributed and were exclusively located along the fibril. A rough estimation of the fibril width revealed that the core of Sup35(1-61) and Ure2(1-80) scaffold co-fibrils was about 5 nm and 6 nm, respectively. A diffuse cloud around the fibrils with a maximal width of 30 nm was also observed, most likely due to the presence of IgG on both sides of the fibril, which was reasonable considering that IgG has a length of 12 nm.

Antibody Binding Capacity of the Nanofibrils

Elevated density of ZZ-domains on the fibril could possibly lead to an increased binding capacity of IgG. Nevertheless, this may also decrease the accessibility of each functional domain due to steric restrictions. In order to identify the doping frequency at which ZZ density impedes IgG binding with respect to binding capacity, fibrils with an increasing molar ratio of un-functional over functional carrier protein were saturated with precisely determined amounts of IgG. Then, the fibrils were pelleted and the absorbance at 280 nm of the supernatant was measured. This allowed the quantification of IgG bound and not bound by the fibrils. According to the collected data, there was a clear correlation between the binding capacity and the fiber composition (FIGS. 5A and 5B and Table 2). Starting from the molar ratio 1:0.04, the IgG binding capacity steadily increased and reached a plateau as the doping frequency approached 1:0.33 (Sup35 fibril) or 1:0.49 (Ure2 fibril). The ratio 1:0.33 for Sup35 fibrils also denoted the maximal overall binding capacity, which was equal to 1.8 mg IgG per mg fibril. The maximal IgG binding capacity of a co-fibril with the ratio of 1:0.04 and 1:0.08 was essentially equimolar to the chimeric proteins, indicating that all binding sites can be accessed. This is the case if about 12 un-functional carrier proteins surround each tethered ZZ molecule in Sup35 co-fibrils (FIG. 5B). Fibrils with higher ZZ content did not grant complete access to each ZZ site, implied by the fact that only a fraction of the theoretical possible amount of IgG was bound. As the ratio increased from 1:0.16 to 1:0.65/0.9 the fraction of accessible ZZ binding sites was linearly decreased (FIG. 5C). The data expressing the number of carrier proteins that were necessary to bind one molecule IgG followed an asymptotic trend and approached 6.5 for Sup35 co-fibrils or 6.0 for Ure2 co-fibrils (FIG. 5B).

Therefore, employing the ZZ-doped nanofibrils for purification of IgG could lead to a higher throughput, which in turn minimizes the overall process time and, thus, could increase cost efficiency.

TABLE 2

IgG binding capacity of Sup35 fibrils that display ZZ

| Sup35:Sup35-ZZ$^A$ | IgG (mg)/ fibril (mg)$^B$ | % of theoretical capacity$^C$ | # proteins/IgG$^D$ |
|---|---|---|---|
| 1:0.04 | 0.68 ± 0.07 | 111 ± 12% | 23.2 ± 2.4 |
| 1:0.08 | 1.14 ± 0.14 | 101 ± 12% | 13.2 ± 1.5 |
| 1:0.16 | 1.43 ± 0.08 | 74 ± 4% | 9.7 ± 0.5 |
| 1:0.24 | 1.67 ± 0.06 | 66 ± 2% | 7.7 ± 0.3 |
| 1:0.33 | 1.77 ± 0.10 | 59 ± 3% | 6.9 ± 0.4 |
| 1:0.41 | 1.72 ± 0.12 | 51 ± 4% | 6.8 ± 0.5 |
| 1:0.49 | 1.72 ± 0.08 | 47 ± 2% | 6.5 ± 0.3 |
| 1:0.57 | 1.67 ± 0.06 | 43 ± 2% | 6.4 ± 0.2 |
| 1:0.65 | 1.61 ± 0.14 | 39 ± 3% | 6.5 ± 0.6 |

$^A$Molar ratio of Sup35(1-61) relative to Sup35(1-61)-ZZ in the co-fibril;
$^B$Average values of the experimentally determined human IgG binding capacity of the respective fibrils;
$^C$Average values of the experimentally determined IgG binding capacity divided by the theoretical maximal binding capacity;
$^D$The number of proteins necessary in order to bind one molecule IgG.
The errors indicated are the standard deviation

TABLE 3

IgG binding capacity of Ure2 fibrils that display ZZ

| Ure2:ZZ-Ure2$^A$ | IgG (mg)/ fibril (mg)$^B$ | % of theoretical capacity$^C$ | # proteins/IgG$^D$ |
|---|---|---|---|
| 1:0.04 | 0.53 ± 0.06 | 102 ± 12% | 25.3 ± 3.3 |
| 1:0.08 | 0.79 ± 0.08 | 82 ± 8% | 16.3 ± 1.6 |
| 1:0.16 | 1.11 ± 0.06 | 66 ± 4% | 10.8 ± 0.7 |
| 1:0.24 | 1.31 ± 0.09 | 59 ± 4% | 8.7 ± 0.6 |
| 1:0.33 | 1.55 ± 0.12 | 58 ± 5% | 7.0 ± 0.6 |
| 1:0.41 | 1.57 ± 0.07 | 52 ± 2% | 6.6 ± 0.3 |
| 1:0.49 | 1.67 ± 0.08 | 51 ± 2% | 6.0 ± 0.3 |
| 1:0.57 | 1.65 ± 0.07 | 46 ± 2% | 5.9 ± 0.3 |
| 1:0.65 | 1.65 ± 0.07 | 44 ± 2% | 5.8 ± 0.3 |

TABLE 3-continued

IgG binding capacity of Ure2 fibrils that display ZZ

| Ure2:ZZ-Ure2$^A$ | IgG (mg)/ fibril (mg)$^B$ | % of theoretical capacity$^C$ | # proteins/IgG$^D$ |
|---|---|---|---|
| 1:0.73 | 1.62 ± 0.05 | 41 ± 1% | 5.7 ± 0.2 |
| 1:0.81 | 1.58 ± 0.06 | 38 ± 1% | 5.8 ± 0.2 |
| 1:0.90 | 1.48 ± 0.06 | 37 ± 3% | 6.1 ± 0.3 |

$^A$Molar ratio of Ure2(1-80) relative to ZZ-Ure2(1-80) in the co-fibril;
$^B$Average values of the experimentally determined human IgG binding capacity of the respective fibrils;
$^C$Average values of the experimentally determined IgG binding capacity divided by the theoretical maximal binding capacity;
$^D$The number of proteins necessary in order to bind one molecule IgG.
The errors indicated are the standard deviation The embodiments described above are to be understood as a few illustrative examples of the present invention. It will be understood by those skilled in the art that various modifications, combinations and changes may be made to the embodiments without departing from the scope of the present invention. In particular, different part solutions in the different embodiments can be combined in other configurations, where technically possible. The scope of the present invention is, however, defined by the appended claims.

REFERENCES

1. Men, D., et al., *Seeding-induced selfassembling protein nanowires dramatically increase the sensitivity of immunoassays.* Nano letters, 2009. 9(6): p. 2246-50.
2. Cheng, X., et al., *Fusion protein linkers: Property, design and functionality.* Advanced Drug Delivery Reviews, 2013. 65: p. 1357-1369.
3. Paushkin, S. V., et al., *Propagation of the yeast prion-like [psi+] determinant is mediated by oligomerization of the SUP35-encoded polypeptide chain release factor.* The EMBO journal, 1996. 15(12): p. 3127-34.
4. Glover, J. R., et al., *Self-seeded fibers formed by Sup35, the protein determinant of [PSI+], a heritable prion-like factor of S. cerevisiae.* Cell, 1997. 89(5): p. 811-9.
5. Maddelein, M. L. and R. B. Wickner, *Two prion-inducing regions of Ure2p are nonoverlapping.* Mol Cell Biol, 1999. 19(6): p. 4516-24.
6. Baldwin, A. J., et al., *Cytochrome Display on Amyloid Fibrils.* Journal of the American Chemical Society, 2006. 128(7): p. 2162-2163.
7. Kodama, H., et al., *Construction of a protein array on amyloid-like fibrils using co-assembly of designed peptides.* Chemical Communications, 2004(24): p. 2876-2877.
8. Sasso, L., et al., *Versatile multi-functionalization of protein nanofibrils for biosensor applications.* Nanoscale, 2014. 6(3): p. 1629-1634.
9. Hudalla, G. A., et al., *Gradated assembly of multiple proteins into supramolecular nanomaterials.* Nature materials, 2014. 13(8): p. 829-36.
10. Padalkar, S., et al., *Alpha-synuclein as a template for the synthesis of metallic nanowires.* Nanotechnology, 2007. 18(5).
11. Zhong, C., et al., *Strong underwater adhesives made by self-assembling multi-protein nanofibres.* Nature Nanotechnology, 2014. 9(10): p. 858-866.
12. Wickner, R. B., F. Dyda, and R. Tycko, *Amyloid of Rnq1p, the basis of the [PIN+] prion, has a parallel in-register beta-sheet structure.* Proc Natl Acad Sci USA, 2008. 105(7): p. 2403-8.

13. Nilsson, B., et al., *A Synthetic Igg-Binding Domain Based on Staphylococcal Protein-A*. Protein Engineering, 1987. 1(2): p. 107-113.
14. Bjorck, L. and G. Kronvall, *Purification and Some Properties of Streptococcal Protein-G, Protein-a Novel lgg-Binding Reagent*. Journal of Immunology, 1984. 133(2): p. 969-974.
15. Eliasson, M., et al., *Chimeric Igg-Binding Receptors Engineered from Staphylococcal Protein-a and Streptococcal Protein-G*. Journal of Biological Chemistry, 1988. 263(9): p. 4323-4327.
16. Grover, R. K., et al., *A Structurally Distinct Human Mycoplasma Protein that Generically Blocks Antigen-Antibody Union*. Science, 2014. 343(6171): p. 656-661.
17. Wikstrom, M., et al., *Proton nuclear magnetic resonance sequential assignments and secondary structure of an immunoglobulin light chain-binding domain of protein L*. Biochemistry, 1993. 32(13): p. 3381-6.
18. Atkins, K. L., et al., *S. aureus IgG-binding proteins SpA and Sbi: Host specificity and mechanisms of immune complex formation*. Molecular Immunology, 2008. 45(6): p. 1600-1611.
19. Åkesson, P., et al., Protein H-A novel igg binding bacterial protein. Molecular Immunology, 1990. 27(6): p. 523-531.
20. Sulaiman, S., et al., *A review: potential usage of cellulose nanofibers (CNF) for enzyme immobilization via covalent interactions*. Appl Biochem Biotechnol, 2015. 175(4): p. 1817-42.
21. Wong, L. S., F. Khan, and J. Micklefield, *Selective covalent protein immobilization: strategies and applications*. Chem Rev, 2009. 109(9): p. 4025-53.
22. Gasteiger, E., et al., *Protein Identification and Analysis Tools on the ExPASy Server*, in *The Proteomics Protocols Handbook*, J. M. Walker, Editor. 2005, Humana Press: Totowa, N.J. p. 571-607.
23. Zhang, L., et al., *Morphology and structure of lipoproteins revealed by an optimized negative-staining protocol of electron microscopy*. Journal of lipid research, 2011. 52(1): p. 175-84.
24. Nilsson, J., et al., *Competitive elution of protein A fusion proteins allows specific recovery under mild conditions*. European journal of biochemistry/FEBS, 1994. 224(1): p. 103-8.
25. Jendeberg, L., et al., *Kinetic analysis of the interaction between protein A domain variants and human Fc using plasmon resonance detection*. Journal of molecular recognition: JMR, 1995. 8(4): p. 270-8.
26. Lee, D. S., et al., *A protein nanofiber hydrogel for sensitive immunoassays*. Analyst, 2013. 138: p. 4786-94.

---

The invention claimed is:

1. An antibody binding nanofibril obtained by co-fibrillation of carrier protein and carrier-Z fusion protein at a molar ratio selected within an interval of from 1:0.20 to 1:0.90, wherein said carrier-Z fusion protein is fusion protein between a carrier protein and an antibody binding Z domain of a protein, wherein the carrier protein is a soluble protein monomer that aggregates into oligomers and further into fibrils and fibers in a molecular self-assembly process.

2. The antibody binding nanofibril according to claim 1, wherein said molar ratio is selected within an interval of from 1:0.30 to 1:0.90.

3. The antibody binding nanofibril according to claim 2, wherein said molar ratio is selected within an interval of from 1:0.30 to 1:0.70.

4. The antibody binding nanofibril according to claim 3, wherein said molar ratio is selected within an interval of from 1:0.30 to 1:0.50.

5. The antibody binding nanofibril according to claim 1, wherein said carrier protein is a Sup35 carrier protein and said carrier-Z fusion protein is a Sup35-Z fusion protein.

6. The antibody binding nanofibril according to claim 5, wherein said Sup35 carrier protein is a N-terminal fragment of *Saccharomyces cerevisiae* eukaryotic translation release factor Sup35 and said Sup35-fusion protein is a fusion protein of said N-terminal fragment of *S. cerevisiae* eukaryotic translation release factor Sup35 and at least one antibody binding Z domain of a protein.

7. The antibody binding nanofibril according to claim 6, wherein said N-terminal fragment consists of amino acids number 1 to 61 of *S. cerevisiae* eukaryotic translation release factor Sup35.

8. The antibody binding nanofibril according to claim 5, wherein said molar ratio is selected within an interval of 1:0.30 to 1:0.40.

9. The antibody binding nanofibril according to claim 8, wherein said molar ratio is selected within an interval of from 1:0.30 to 1:0.35.

10. The antibody binding nanofibril according to claim 9, wherein said molar ratio is equal to about 1:0.33.

11. The antibody binding nanofibril according to claim 1, wherein said carrier protein is a Ure2 carrier protein and said carrier-Z fusion protein is a Ure2-Z fusion protein.

12. The antibody binding nanofibril according to claim 11, wherein said Ure2 carrier protein is an N-terminal fragment of *Saccharomyces cerevisiae* ureidosuccinate transport protein and said Ure2-Z fusion protein is a fusion protein of said N-terminal fragment of *S. cerevisiae* ureidosuccinate transport protein and at least one antibody binding Z domain of a protein.

13. The antibody binding nanofibril according to claim 12, wherein said N-terminal fragment consists of amino acids number 1 to 80 of *S. cerevisiae* ureidosuccinate transport protein.

14. The antibody binding nanofibril according to claim 11, wherein said molar ratio is selected within an interval of 1:0.45 to 1:0.55.

15. The antibody binding nanofibril according to claim 14, wherein said molar ratio is selected within an interval of from 1:0.47 to 1:0.51.

16. The antibody binding nanofibril according to claim 15, wherein said molar ratio is equal to about 1:0.49.

17. The antibody binding nanofibril according to claim 1, wherein said carrier-Z fusion protein is a fusion protein between said carrier protein and an immunoglobulin G (IgG) binding domain of protein A.

18. The antibody binding nanofibril according to claim 1, wherein said carrier-Z fusion protein is a carrier-Z dimer fusion protein, wherein said carrier-Z dimer fusion protein is a fusion protein between a carrier protein and two antibody binding Z domains of a protein.

19. The antibody binding nanofibril according to claim 1, wherein said antibody binding nanofibril is capable of binding immunoglobulin G (IgG).

20. The antibody binding nanofibril according to claim 1, wherein said antibody binding nanofibril has a binding capacity of at least 1.5 mg immunoglobulin G (IgG) per mg nanofibril.

21. The antibody binding nanofibril according to claim 20, wherein said antibody binding nanofibril has a binding capacity of at least 1.6 mg IgG per mg nanofibril.

22. The antibody binding nanofibril according to claim 21, wherein said antibody binding nanofibril has a binding capacity of at least 1.7 mg IgG per mg nanofibril.

23. The antibody binding nanofibril according to claim 22, wherein said antibody binding nanofibril has a binding capacity of at least 1.8 mg IgG per mg nanofibril.

24. The antibody binding nanofibril according to claim 1, comprising at least one antibody bound to at least one antibody binding Z domain of the carrier-Z fusion protein.

25. A kit for detecting presence of a chemical substance in a sample, said kit comprises:
   antibody binding nanofibrils according to claim 1; and
   antibodies that specifically bind to said chemical substance in said sample, wherein carrier-Z fusion protein of said antibody binding nanofibrils is capable of binding said antibodies.

26. An antibody capturing device comprising antibody binding nanofibrils according to claim 1 immobilized onto a solid surface.

27. A method of producing an antibody binding nanofibril, said method comprising co-fibrillating carrier protein and carrier-Z fusion protein at a molar ratio selected within an interval of from 1:0.20 to 1:0.90 to form said antibody binding nanofibril, wherein said carrier-Z fusion protein is fusion protein between a carrier protein and antibody binding Z domain.

28. The method according to claim 27, wherein, prior to co-fibrillating the carrier protein and the carrier-Z fusion protein, the method comprises producing seeds by sonicating a first portion of the carrier protein in an aqueous solution, and
   wherein co-fibrillating said carrier protein and said carrier-Z fusion protein comprises incubating said seeds with a second portion of said carrier protein and said carrier-Z fusion protein, with the carrier protein and the carrier-Z fusion protein at said molar ratio to form said antibody binding nanofibril.

29. The antibody binding nanofibril according to claim 1, wherein said antibody binding Z domain is an antibody binding domain of a protein selected from the group consisting of protein A, protein G, protein A/G, protein M, protein L, SpA, Sbi, and protein H.

30. The antibody binding nanofibril according to claim 1, wherein said antibody binding Z domain is capable of binding immunoglobulin G (IgG).

* * * * *